US012594429B2

(12) United States Patent
Zenisek et al.

(10) Patent No.: US 12,594,429 B2
(45) Date of Patent: Apr. 7, 2026

(54) STIMULATION PROGRAMMING AND CONTROL BASED ON PATIENT AMBULATORY VELOCITY

(71) Applicant: Medtronic, Inc., Minneapolis, MN (US)

(72) Inventors: Todd D. Zenisek, Georgetown, TX (US); Nathan A. Torgerson, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 517 days.

(21) Appl. No.: 17/664,363

(22) Filed: May 20, 2022

(65) Prior Publication Data

US 2022/0387803 A1 Dec. 8, 2022

Related U.S. Application Data

(60) Provisional application No. 63/196,213, filed on Jun. 2, 2021.

(51) Int. Cl.
*A61N 1/36* (2006.01)
*G01S 17/58* (2006.01)
(52) U.S. Cl.
CPC ..... *A61N 1/36167* (2013.01); *A61N 1/36135* (2013.01); *A61N 1/36192* (2013.01); *G01S 17/58* (2013.01)
(58) Field of Classification Search
CPC ............ A61N 1/36167; A61N 1/36135; A61N 1/36192; G01S 17/58
See application file for complete search history.

(56) References Cited

U.S. PATENT DOCUMENTS

| | | | |
|---|---|---|---|
| 9,002,472 B2 | 4/2015 | Kokones et al. | |
| 9,522,278 B1 * | 12/2016 | Heldman | ................. A61B 5/11 |
| 10,478,626 B1 | 11/2019 | Heldman et al. | |
| 10,625,074 B2 | 4/2020 | Rosenbluth et al. | |

(Continued)

FOREIGN PATENT DOCUMENTS

WO 2020049514 A1 3/2020

OTHER PUBLICATIONS

Response to Extended Search Report dated Oct. 10, 2022, from counterpart European Application No. 22176710.6 filed May 15, 2023, 8 pp.

(Continued)

*Primary Examiner* — Jennifer Pitrak McDonald
*Assistant Examiner* — Jennifer L Ghand
(74) *Attorney, Agent, or Firm* — Shumaker & Sieffert, P.A.

(57) ABSTRACT

A method includes receiving, with one or more processors, a first ambulatory velocity information of a patient while electrical stimulation with a first set of stimulation parameters is being delivered to the patient; adjusting, based on the first ambulatory velocity information and by a predetermined amount, one or more of the first set of stimulation parameters to generate an adjusted set of stimulation parameters by a predetermined amount; receiving, with the one or more processors, a subsequent ambulatory velocity information of the patient while the electrical stimulation with an adjusted set of stimulation parameters is being delivered to the patient; and generating, with the one or more processors and based on the subsequent ambulatory velocity, one or more recommended electrical stimulation parameters the patient.

15 Claims, 9 Drawing Sheets

(56) References Cited

U.S. PATENT DOCUMENTS

| | | | | |
|---|---|---|---|---|
| 10,786,199 | B1 | 9/2020 | Giuffrida et al. | |
| 2008/0269812 | A1* | 10/2008 | Gerber | A61N 1/36514 |
| | | | | 607/2 |
| 2009/0118786 | A1* | 5/2009 | Meadows | A61B 5/1126 |
| | | | | 607/45 |
| 2010/0010380 | A1* | 1/2010 | Panken | A61B 5/1116 |
| | | | | 600/587 |
| 2012/0277833 | A1* | 11/2012 | Gerber | A61N 1/36139 |
| | | | | 607/62 |
| 2013/0274830 | A1 | 10/2013 | Skelton | |
| 2014/0371544 | A1 | 12/2014 | Wu et al. | |
| 2017/0080151 | A1 | 3/2017 | Cerny et al. | |
| 2022/0203096 | A1* | 6/2022 | Crawford | A61N 1/36003 |
| 2022/0387803 | A1* | 12/2022 | Zenisek | A61N 1/36167 |

OTHER PUBLICATIONS

Bazarevsky et al., "On-device, Real-time Body Pose Tracking with MediaPipe BlazePose", Google AI Blog, Aug. 13, 2020, 6 pp.

Borzi et al., "Home monitoring of motor fluctuations in Parkinson's disease patients", Journal of Reliable Intelligent Environments, vol. 5, No. 3, Jul. 2, 2019, pp. 145-162.

Wang et al., "Use of surface electromyography to assess and select patients with idiopathic dystonia for bilateral pallidal stimulatio", Journal of neurosurgery, vol. 105, No. 1, Jul. 2006, pp. 21-25.

Iervolino et al., "A SensorTile mounted on the right ankle of an athlete's foot. Positive directions of the accelerometer local axes are indicated", ResearchGate.com, 7 pp., Retrieved from the Internet on Jun. 7, 2022 from URL: www.researchgate.net /figure/A-SensorTile-mounted-on-the-right-ankle-of-an-athletes-foot-Positive-directions-of-the_fig11_320649673.

FREEEMG, "Surface electromyography device with wireless probes for the dynamic analysis of muscle activity", BTS Bioengineering, 9 pp., Retrieved from the Internet on Jun. 8, 2022 from URL: https://www.btsbioengineering.com/products/freeemg-surfaceemg-semg/.

Extended Search Report from counterpart European Application No. 22176710.6 dated Oct. 10, 2022, 7 pp.

* cited by examiner

10

300

400

424

422

426

428

600

DIRECT DELIVERY STIMULATION TO PATIENT

602

RECEIVE VELOCITY INFORMATION

604

GENERATE OUTPUT BASED ON RECEIVED VELOCITY
INFORMATION

STIMULATION PROGRAMMING AND CONTROL BASED ON PATIENT AMBULATORY VELOCITY

This application claims the benefit of U.S. Provisional Patent Application No. 63/196,213, filed 2 Jun. 2021, the entire contents of which is incorporated herein by reference.

TECHNICAL FIELD

This disclosure generally relates to medical devices, and more specifically, electrical stimulation.

BACKGROUND

Electrical stimulation devices may be external to or implanted within a patient, and configured to deliver electrical stimulation therapy to various tissue sites to treat a variety of symptoms or conditions such as chronic pain, tremor, Parkinson's disease, epilepsy, or other neurological disorders, urinary or fecal incontinence, sexual dysfunction, obesity, or gastroparesis. An electrical stimulation device may deliver electrical stimulation therapy via electrodes, e.g., carried by one or more leads, positioned proximate to target locations associated with the brain, the spinal cord, pelvic nerves, tibial nerves, peripheral nerves, the gastrointestinal tract, or elsewhere within a patient. Stimulation within the brain, proximate the spinal cord, proximate the sacral nerve, and proximate peripheral nerves is often referred to as deep brain stimulation (DBS), spinal cord stimulation (SCS), sacral neuromodulation (SNM), and peripheral nerve stimulation (PNS), respectively.

A physician or clinician may select values for a number of programmable stimulation parameters in order to define the electrical stimulation therapy to be delivered by the implantable stimulator to a patient. For example, the physician or clinician may select one or more electrodes, polarities of selected electrodes, a voltage or current amplitude, a pulse width, and a pulse frequency as stimulation parameters. A set of therapy stimulation parameters, such as a set including electrode combination, electrode polarity, amplitude, pulse width and pulse frequency, may be referred to as a therapy program in the sense that they define the electrical stimulation therapy to be delivered to the patient.

SUMMARY

In general, the disclosure describes techniques for stimulation efficacy evaluation, programming and/or control based on information relating to sensed patient velocity. In some examples, sensed velocity information may be used to evaluate efficacy of stimulation or stimulation parameters, such as stimulation amplitude, stimulation pulse width, stimulation pulse rate, and/or stimulation cycling, assist a user in evaluating efficacy of one or more of such stimulation parameters, assist a user in programming one or more of such stimulation parameters, and/or automatically control one or more of such stimulation parameters, e.g., on a closed loop basis.

A neurostimulation device, external programmer, or remote programming device may receive velocity information relating to velocity values from one or more velocity sensing devices, either directly or via network connections, and perform, direct or control, based on the velocity information, generation of neurostimulation efficacy information, information to assist in programming of one or more neurostimulation stimulation parameters, and/or automatic control of one or more stimulation parameters. In this manner, a stimulation device, external programmer, or remote programming device may select, adjust or control one or more stimulation parameters based on the sensed velocity information to eliminate or alleviate, or delay the onset of, symptoms of a disease, disorder or syndrome.

In one example, a method includes receiving, with one or more processors, a first ambulatory velocity information of a patient while electrical stimulation with a first set of stimulation parameters is being delivered to the patient; adjusting, based on the first ambulatory velocity information and by a predetermined amount, one or more of the first set of stimulation parameters to generate an adjusted set of stimulation parameters by a predetermined amount; receiving, with the one or more processors, a subsequent ambulatory velocity information of the patient while the electrical stimulation with an adjusted set of stimulation parameters is being delivered to the patient; and generating, with the one or more processors and based on the subsequent ambulatory velocity, one or more recommended electrical stimulation parameters for the patient.

In another example, a device includes process circuitry configured to: receive, with one or more processors, a first ambulatory velocity information of a patient while electrical stimulation with a first set of stimulation parameters is being delivered to the patient; adjust, based on the first ambulatory velocity information and by a predetermined amount, one or more of the first set of stimulation parameters to generate an adjusted set of stimulation parameters by a predetermined amount; receive, with the one or more processors, a subsequent ambulatory velocity information of the patient while the electrical stimulation with an adjusted set of stimulation parameters is being delivered to the patient; and generate, with the one or more processors and based on the subsequent ambulatory velocity, one or more recommended electrical stimulation parameters the patient.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

DETAILED DESCRIPTION

Efficacy of brain stimulation in eliminating or alleviating symptoms, or preventing or delaying onset or progression of aspects of, a disease, disorder or syndrome, may vary according to the stimulation parameters used to deliver the stimulation to a patient. Selection of level of amplitude of the stimulation, as one example, can elicit a desired response to the stimulation.

This disclosure describes techniques for programming and/or control based on information relating to sensed patient ambulatory velocity information. In some examples, sensed patient ambulatory velocity information may be used to evaluate efficacy of stimulation or stimulation parameters, such as stimulation amplitude, pulse width, pulse rate, or cycling, assist a user in programming one or more of such stimulation parameters, and/or automatically control one or more of such stimulation parameters, e.g., on a closed loop basis. Using the sensed ambulatory velocity information to confirm device programming provides objective feedback to the clinician without requiring feedback from the patient. In addition, the feedback from the sensed velocity information allows for objective, quantitative, patient-specific feedback for the clinician without having to engage or prompt the patient. This quantitative, patient specific data may also assist in the demonstration of medication adjustment changes, disease state progression, etc. (e.g., regardless of clinician programming experience).

Figure 1:
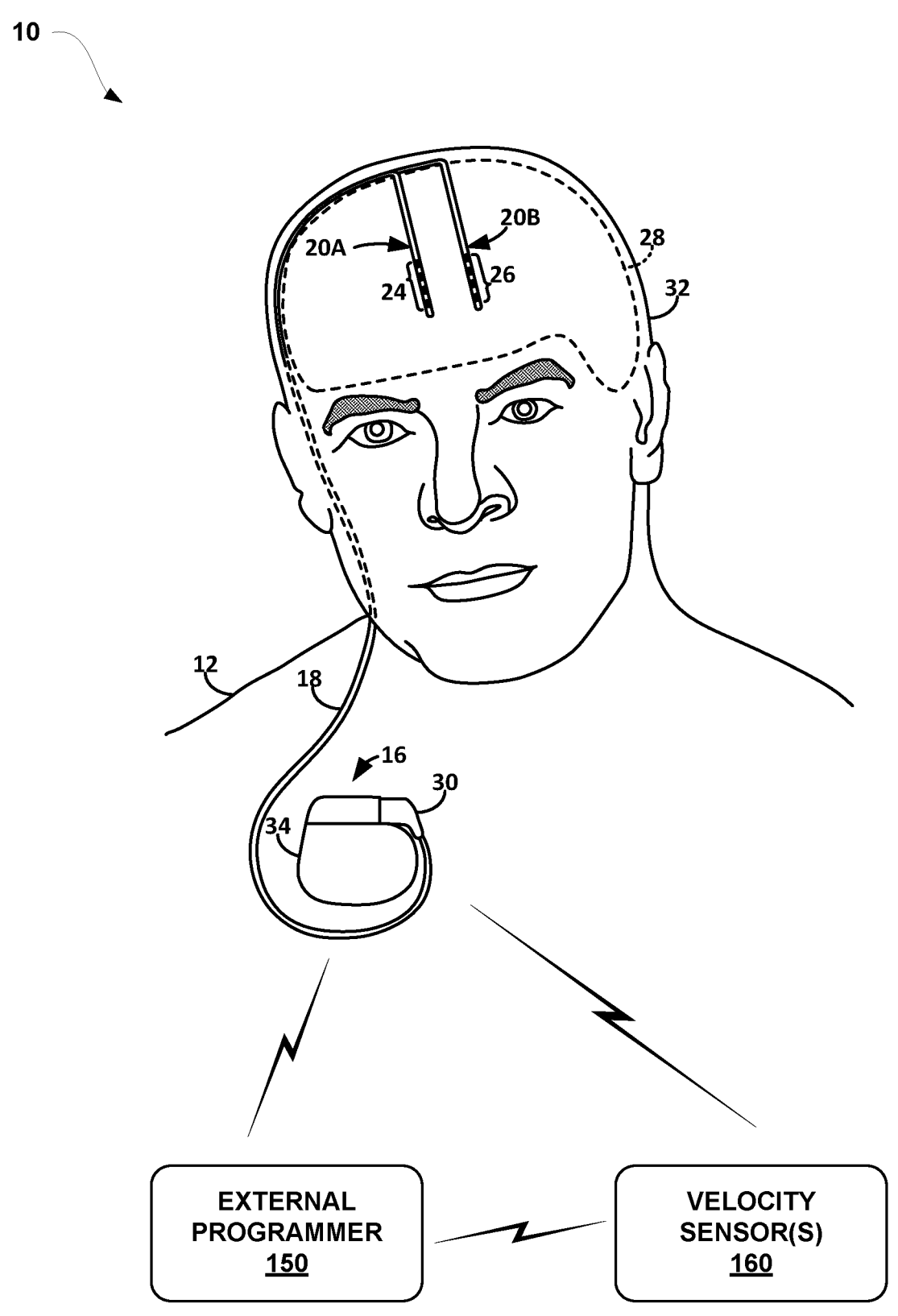
FIG. 1 is a conceptual diagram illustrating an example deep brain stimulation (DBS) system that includes an implantable medical device (IMD) configured to sense a bioelectrical brain signal and deliver electrical stimulation therapy to a tissue site within a brain of a patient, an external programmer, and one or more velocity sensors in accordance with one or more techniques of this disclosure.

Systems and methods for stimulation efficacy evaluation, programming and/or control based on information relating to sensed patient ambulatory velocity are described herein. The system may include a stimulator system that interacts with a stimulator programmer, along with a velocity detecting device. FIG. 1 is a conceptual diagram illustrating an example system 100 that includes an implantable medical device (IMD) 16 configured to deliver deep brain stimulation (DBS) therapy, programmer 140, an external programmer 150, and one or more velocity sensors 160, in accordance with one or more examples of this disclosure. Processing circuitry 140 may include one or more processors configured to perform various operations of IMD 16. Although the examples described in this disclosure are generally applicable to a variety of medical devices including external devices and IMDs, application of such techniques to IMDs and, more particularly, implantable electrical stimulators will be described for purposes of illustration. The system may not be a fully implanted system where the pulse generator is external to the patient and stimulation is transmitted transdermally (e.g., through the skin).

In the example shown in FIG. 1, therapy system 10 includes medical device programmer 150, implantable medical device (IMD) 16, lead extension 18, and one or more leads 20A and 20B (collectively "leads 20") with respective sets of electrodes 24, 26. IMD 16 includes a therapy module that includes a stimulation generator that is configured to generate and deliver electrical stimulation therapy to one or more regions of brain 28 of patient 12 via a subset of electrodes 24, 26 of leads 20A and 20B, respectively. In the example shown in FIG. 1, therapy system 10 may be referred to as a deep brain stimulation (DBS) system because IMD 16 provides electrical stimulation therapy directly to tissue within brain 28, e.g., a tissue site under the dura mater of brain 28 or one or more branches or nodes, or a confluence of fiber tracks. In other examples, leads 20 may be positioned to deliver therapy to a surface of brain 28 (e.g., the cortical surface of brain 28). In some examples, IMD 16 may provide cortical stimulation therapy to patient 12, e.g., by delivering electrical stimulation to one or more tissue sites in the cortex of brain 28. In some examples, IMD 16 may provide vagal nerve stimulation (VNS) therapy to patient 12 by delivering electrical stimulation to one or more vagal nerve tissue sites. In some examples, IMD 16 may provide spinal cord stimulation (SCS) therapy to patient 12 by delivering electrical stimulation to one or more spinal nerves.

Although electrical stimulation therapy is primarily referred to throughout the remainder of the application, in other examples, therapy system 10 may be configured to deliver other types of therapy in addition to or instead of electrical stimulation therapy, such as, e.g., drug delivery therapy.

In the example shown in FIG. 1, IMD 16 may be implanted within a subcutaneous pocket in the pectoral region of patient 12. In other examples, IMD 16 may be implanted within other regions of patient 12, such as a subcutaneous pocket in the abdomen or buttocks of patient 12 or proximate the cranium of patient 12. Implanted lead extension 18 is coupled to IMD 16 via connector block 30 (also referred to as a header), which may include, for example, electrical contacts that electrically couple to respective electrical contacts on lead extension 18. The electrical contacts electrically couple the electrodes 24, 26 carried by leads 20 to IMD 16. Lead extension 18 traverses from the implant site of IMD 16 within a chest cavity of patient 12, along the neck of patient 12 and through the cranium of patient 12 to access brain 28. IMD 16 can be constructed of a biocompatible material that resists corrosion and degradation from bodily fluids. IMD 16 may comprise a hermetic housing 34 to substantially enclose components, such as a processor, therapy module, and memory.

In the example shown in FIG. 1, leads 20 are implanted within the right and left hemispheres, respectively, of brain 28 in order to deliver electrical stimulation to one or more regions of brain 28, which may be selected based on many factors, such as the type of patient condition for which therapy system 10 is implemented to manage. Other implant sites for leads 20 and IMD 16 are contemplated. For example, IMD 16 may be implanted on or within cranium 32 or leads 20 may be implanted within the same hemisphere at multiple target tissue sites or IMD 16 may be coupled to a single lead that is implanted in one or both hemispheres of brain 28.

Leads 20 may be positioned to deliver electrical stimulation to one or more target tissue sites within brain 28 to manage patient symptoms associated with a disorder of patient 12. Leads 20 may be implanted to position electrodes 24, 26 at desired locations of brain 28 through respective holes in cranium 32. Leads 20 may be placed at any location within brain 28 such that electrodes 24, 26 are capable of providing electrical stimulation to target tissue sites within brain 28 during treatment. Different neurological or psychiatric disorders may be associated with activity in one or more of regions of brain 28, which may differ between patients. For example, a suitable target therapy delivery site within brain 28 for controlling a movement disorder of patient 12 may include one or more of the pedunculopontine nucleus (PPN), thalamus, basal ganglia structures (e.g., globus pallidus, substantia nigra or subthalamic nucleus), zona inserta, fiber tracts, lenticular fasciculus (and branches thereof), ansa lenticularis, and/or the Field of Forel (thalamic fasciculus). The PPN may also be referred to as the pedunculopontine tegmental nucleus.

As another example, in the case of MDD, bipolar disorder, OCD, or other anxiety disorders, leads 20 may be implanted to deliver electrical stimulation to the anterior limb of the internal capsule of brain 28, and only the ventral portion of the anterior limb of the internal capsule (also referred to as a VC/VS), the subgenual component of the cingulate cortex (which may be referred to as CG25), anterior cingulate cortex Brodmann areas 32 and 24, various parts of the prefrontal cortex, including the dorsal lateral and medial pre-frontal cortex (PFC) (e.g., Brodmann area 9), ventro-medial prefrontal cortex (e.g., Brodmann area 10), the lateral and medial orbitofrontal cortex (e.g., Brodmann area 11), the medial or nucleus accumbens, thalamus, intralaminar thalamic nuclei, amygdala, hippocampus, the lateral hypothalamus, the Locus ceruleus, the dorsal raphe nucleus, ventral tegmentum, the substantia nigra, subthalamic nucleus, the inferior thalamic peduncle, the dorsal medial nucleus of the thalamus, the habenula, the bed nucleus of the stria terminalis, or any combination thereof. Target tissue sites not located in brain 28 of patient 12 are also contemplated.

As another example, in the case of a seizure disorder or Alzheimer's disease, for example, leads 20 may be implanted to deliver electrical stimulation to regions within the Circuit of Papez, such as, e.g., the anterior thalamic nucleus, the internal capsule, the cingulate, the fornix, the mammillary bodies, the mammillothalamic tract (mammillothalamic fasciculus), and/or hippocampus. For example, in the case of a seizure disorder, IMD 16 may deliver therapy to a region of brain 28 via a selected subset of electrodes 24, 26 to suppress cortical activity within the anterior thalamic nucleus, hippocampus, or other brain region associated with the occurrence of seizures (e.g., a seizure focus of brain 28). Conversely, in the case of Alzheimer's disease, IMD 16 may deliver therapy to a region of brain 28 via electrodes 24, 26 to increase cortical activity within the anterior thalamic nucleus, hippocampus, or other brain region associated with Alzheimer's disease. As another example, in the case of depression (e.g., MDD), IMD 16 may deliver therapy to a region of brain 28 via electrodes 24, 26 to increase cortical activity within one or more regions of brain 28 to effectively treat the patient disorder. As another example, IMD 16 may deliver therapy to a region of brain 28 via electrodes 24, 26 to decrease cortical activity within one or more regions of brain 28, such as, e.g., the frontal cortex, to treat the disorder.

Although leads 20 are shown in FIG. 1 as being coupled to a common lead extension 18, in other examples, leads 20 may be coupled to IMD 16 via separate lead extensions or directly coupled to IMD 16. Moreover, although FIG. 1 illustrates system 10 as including two leads 20A and 20B coupled to IMD 16 via lead extension 18, in some examples, system 10 may include one lead or more than two leads.

Leads 20 may be implanted within a desired location of brain 28 via any suitable technique, such as through respective burr holes in the skull of patient 12 or through a common burr hole in the cranium 32. Leads 20 may be placed at any location within brain 28 such that electrodes 24, 26 of leads 20 are capable of providing electrical stimulation to targeted tissue during treatment. Electrical stimulation generated from the stimulation generator (not shown) within the therapy module of IMD 16 may help mitigate the symptoms of movement disorders, such as by improving the performance of motor tasks by patient 12 that may otherwise be difficult. These tasks may include, for example, at least one of initiating movement, maintaining movement, grasping and moving objects, improving gait and balance associated with narrow turns, and the like. The exact therapy parameter values of the electrical stimulation therapy that may help mitigate symptoms of the movement disorder (or other patient condition) may be specific for the particular target stimulation site (e.g., the region of the brain) involved as well as the particular patient and patient condition.

In the examples shown in FIG. 1, electrodes 24, 26 of leads 20 are shown as ring electrodes. Ring electrodes may be relatively easy to program and are typically capable of delivering an electrical field to any tissue adjacent to leads 20. In other examples, electrodes 24, 26 of leads 20 may have different configurations. For example, electrodes 24, 26 of leads 20 may have a complex electrode array geometry that is capable of producing shaped electrical fields, including interleaved stimulation. An example of a complex electrode array geometry may include an array of electrodes positioned at different axial positions along the length of a lead, as well as at different angular positions about the periphery, e.g., circumference, of the lead. The complex electrode array geometry may include multiple electrodes (e.g., partial ring or segmented electrodes) around the perimeter of each lead 20, in addition to, or instead of, a ring electrode. In this manner, electrical stimulation may be directed to a specific direction from leads 20 to enhance therapy efficacy and reduce possible adverse side effects from stimulating a large volume of tissue. In some examples in which multiple leads 20 are implanted on the same hemisphere surrounding a target, steered electrical stimulation can be performed in between two or more electrodes.

In some examples, outer housing 34 of IMD 16 may include one or more stimulation and/or sensing electrodes. For example, housing 34 can comprise an electrically conductive material that is exposed to tissue of patient 12 when IMD 16 is implanted in patient 12, or an electrode can be attached to housing 34. In other examples, leads 20 may have shapes other than elongated cylinders as shown in FIG. 1 with active or passive tip configurations. For example, leads 20 may be paddle leads, spherical leads, bendable leads, or any other type of shape effective in treating patient 12.

IMD 16 may deliver electrical stimulation therapy to brain 28 of patient 12 according to one or more stimulation therapy programs. A stimulation therapy program may define one or more electrical stimulation parameter values for therapy generated by a therapy module of IMD 16 and delivered from IMD 16 to brain 28 of patient 12. Where IMD 16 delivers electrical stimulation in the form of electrical pulses, for example, the electrical stimulation parameters may include amplitude mode (constant current or constant voltage with or without multiple independent paths), pulse amplitude, pulse rate, pulse width, a waveform shape, and cycling parameters (e.g., with or without cycling, duration of cycling, and the like). In addition, if different electrodes are available for delivery of stimulation, a therapy parameter of a therapy program may be further characterized by an electrode combination, which may define selected electrodes and their respective polarities.

In some examples, IMD 16 is configured to deliver electrical stimulation therapy to brain 28 of patient 12 in an open loop manner, in which IMD 16 delivers the stimulation therapy without intervention from a user or a sensor. In other examples, IMD 16 is configured to deliver electrical stimulation therapy to brain 28 of patient 12 in a closed loop manner or a pseudo-closed loop manner, in which IMD 16 controls the timing of the delivery of electrical stimulation to brain 28, the output parameters of the electrical stimulation, or both based on one or more of user input and input from a sensor. The sensor may, for example, provide feedback that may be used to control the electrical stimulation output from IMD 16.

In addition to being configured to deliver therapy to manage a disorder of patient 12, therapy system 10 is configured to sense bioelectrical brain signals of patient 12. For example, IMD 16 may include a sensing module that is configured to sense bioelectrical brain signals within one or more regions of brain 28 via a subset of electrodes 24, 26, another set of electrodes, or both. Accordingly, in some examples, electrodes 24, 26 may be used to deliver electrical stimulation from the therapy module to target sites within brain 28 as well as sense brain signals within brain 28. However, IMD 16 can also use a separate set of sensing electrodes to sense the bioelectrical brain signals. In the example shown in FIG. 1, the signals generated by electrodes 24, 26 are conducted to the sensing module within IMD 16 via conductors within the respective lead 20A, 20B. In some examples, the sensing module of IMD 16 may sense bioelectrical brain signals via one or more of the electrodes 24, 26 that are also used to deliver electrical stimulation to brain 28. In other examples, one or more of electrodes 24, 26 may be used to sense bioelectrical brain signals while one or more different electrodes 24, 26 may be used to deliver electrical stimulation.

Depending on the particular stimulation electrodes and sense electrodes used by IMD 16, IMD 16 may monitor bioelectrical brain signals and deliver electrical stimulation at the same region of brain 28 or at different regions of brain 28. In some examples, the electrodes used to sense bioelectrical brain signals may be located on the same lead used to deliver electrical stimulation, while in other examples, the electrodes used to sense bioelectrical brain signals may be located on a different lead than the electrodes used to deliver electrical stimulation. In some examples, a bioelectrical brain signal of patient 12 may be monitored with external electrodes, e.g., scalp electrodes. Moreover, in some examples, the sensing module that senses bioelectrical brain signals of brain 28 (e.g., the sensing module that generates an electrical signal indicative of the activity within brain 28) is in a physically separate housing from outer housing 34 of IMD 16. However, in the example shown in FIG. 1 and the example primarily referred to herein for ease of description, the sensing module and therapy module of IMD 16 are enclosed within a common outer housing 34.

The bioelectrical brain signals sensed by IMD 16 may reflect changes in electrical current produced by the sum of electrical potential differences across brain tissue. Example bioelectrical brain signals include, but are not limited to, an electroencephalogram (EEG) signal, an electrocorticogram (ECoG) signal, a LFP sensed from within one or more regions of a patient's brain, and/or action potentials from single cells within the patient's brain. In some examples, LFP data can be measured ipsilaterally or contralaterally and considered as an average (e.g., a maximum or minimum or a heuristic combination thereof) or as some other value. The location at which the signals are obtained may be adjusted to a disease onset side of the body of patient 12 or severity of symptoms or disease duration. The adjustments, may, for example, be made on the basis of clinical symptoms presented and their severity, which can be augmented or annotated with recorded LFP data. A clinician or a processor of IMD 16 may also add heuristic weights to ipsilaterally and/or contralaterally measured LFP data to be considered for system feedback.

Sensed bioelectrical brain signals of patient 12 may generate brain signal information and may be used to determine the patient state of patient 12, for example upon delivery of electrical stimulation. The patient state can be, for example, a patient disease state, a state in which a symptom of a patient condition is observed, or a patient state indicative of the efficacy of therapy delivered by a medical device or the efficacy of medication.

In some examples, the processor generates an indication of the determined patient state, controls therapy delivery to the patient based on the determined patient state, monitors a patient condition based on the determined patient state, generates a patient diagnosis (e.g., determines a patient condition sub-type) based on the determined patient state, or any combination thereof. For example, the processor can control therapy delivery by, for example, modifying one or more therapy parameter values based on the determined patient state. One or more therapy parameter values may be controlled in order to increase or decrease the intensity of therapy delivery (e.g., by increasing or decreasing one or more of the frequency, amplitude, or other stimulation parameter values), to initiate delivery of electrical stimulation, by IMD 16, to a target therapy delivery site in patient 12, or, depending on the type of therapy delivery, to terminate delivery of electrical stimulation to the target therapy delivery site.

The processor may modify the therapy delivered by IMD 16 using any suitable technique. In some examples, the processor modifies therapy by at least modifying at least one therapy parameter value with which IMD 16 generates and delivers therapy to patient 12. The at least one therapy parameter value may be a part of a therapy program that defines values for a plurality of therapy parameters. As a result, in some examples, the processor may modify at least one therapy parameter value by at least modifying a therapy program (e.g., changing the value of at least one therapy parameter of the therapy program or selecting a new therapy program).

In some examples, IMD 16 may be configured to sense the bioelectrical brain signal (e.g., by measuring an LFP) at periodic, predetermined (which may also be periodic), or random intervals, or in response to a patient input or another trigger. In other examples, IMD 16 continuously senses the bioelectrical brain signal, but the processor only samples the sensed bioelectrical brain signal (e.g., the last stored bioelectrical brain signal) and determines whether the sample includes the biomarker at predetermined periodic times or in response to user input (e.g., input/trigger from a patient).

External programmer 150 is configured to wirelessly communicate with IMD 16 as needed to provide or retrieve therapy information. Programmer 150 is an external computing device that the user, e.g., the clinician and/or patient 12, may use to communicate with IMD 16. For example, programmer 150 may be a clinician programmer that the clinician uses to communicate with IMD 16 and program one or more therapy programs for IMD 16. In addition, or instead, programmer 150 may be a patient programmer that allows patient 12 to select programs, view and modify therapy parameter values, and/or stop the stimulation for example due to side effects. The clinician programmer may include more programming features than the patient programmer. In other words, more complex or sensitive tasks may only be allowed by the clinician programmer to prevent an untrained patient from making undesired changes to IMD 16.

Programmer 150 may be a hand-held computing device with a display viewable by the user and an interface for providing input to programmer 150 (i.e., a user input mechanism). For example, programmer 150 may include a small display screen (e.g., a liquid crystal display (LCD) or a light emitting diode (LED) display) that presents information to the user. In addition, programmer 150 may include a touch screen display, keypad, buttons, a peripheral pointing device or another input mechanism that allows the user to navigate through the user interface of programmer 150 and provide input. If programmer 150 includes buttons and a keypad, the buttons may be dedicated to performing a certain function, i.e., a power button, the buttons and the keypad may be soft keys that change in function depending upon the section of the user interface currently viewed by the user, or any combination thereof. Alternatively, the screen (not shown) of programmer 150 may be a touch screen that allows the user to provide input directly to the user interface shown on the display. The user may use a stylus or their finger to provide input to the display.

In other examples, programmer 150 may be a larger workstation or a separate application within another multi-function device, rather than a dedicated computing device. For example, the multi-function device may be a notebook computer, tablet computer, workstation, cellular phone, personal digital assistant or another computing device that may run an application that enables the computing device to operate as a secure medical device programmer 150. A wireless adapter coupled to the computing device may enable secure communication between the computing device and IMD 16.

When programmer 150 is configured for use by the clinician, programmer 150 may be used to transmit initial programming information to IMD 16. This initial information may include hardware information, such as the type of leads 20, the arrangement of electrodes 24, 26 on leads 20, the position of leads 20 within brain 28, initial programs defining therapy parameter values, and any other information that may be useful for programming into IMD 16. Programmer 150 may also be capable of completing functional tests (e.g., measuring the impedance of electrodes 24, 26 of leads 20).

The clinician may also generate and store therapy programs within IMD 16 with the aid of programmer 150. During a programming session, the clinician may determine one or more therapy programs that may provide efficacious therapy to patient 12 to address symptoms associated with the movement disorder (or other patient conditions). For example, the clinician may select one or more electrode combinations with which stimulation is delivered to brain 28. During the programming session, patient 12 may provide feedback to the clinician as to the efficacy of the specific program being evaluated or the clinician may evaluate the efficacy based on one or more sensed or observable physiological parameters of patient (e.g., muscle activity) or based on motion detected via one or more motion sensors that generate signals indicative of motion of patient 12. Programmer 150 may assist the clinician in the creation/ identification of therapy programs by providing a methodical system for identifying potentially beneficial therapy parameter values.

Programmer 150 may also be configured for use by patient 12. When configured as a patient programmer, programmer 150 may have limited functionality (compared to a clinician programmer) in order to prevent patient 12 from altering critical functions of IMD 16 or applications that may be detrimental to patient 12.

Whether programmer 150 is configured for clinician or patient use, programmer 150 is configured to communicate to IMD 16 and, optionally, another computing device, via wireless communication. Programmer 150, for example, may communicate via wireless communication with IMD 16 using radio frequency (RF) telemetry techniques known in the art. Programmer 150 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 150 may also communicate with other programming or computing devices via exchange of removable media, such as magnetic or optical disks, memory cards or memory sticks. Further, programmer 150 may communicate with IMD 16 and another programmer via remote telemetry techniques known in the art, communicating via a local area network (LAN), wide area network (WAN), public switched telephone network (PSTN), or cellular telephone network, for example.

Therapy system 10 may be implemented to provide chronic stimulation therapy to patient 12 over the course of several months or years. However, system 10 may also be employed on a trial basis to evaluate therapy before committing to full implantation. If implemented temporarily, some components of system 10 may not be implanted within patient 12. For example, patient 12 may be fitted with an external medical device, such as a trial stimulator, rather than IMD 16. The external medical device may be coupled to percutaneous leads or to implanted leads via a percutaneous extension. If the trial stimulator indicates DBS system 10 provides effective treatment to patient 12, the clinician may implant a chronic stimulator within patient 12 for relatively long-term treatment.

System 10 shown in FIG. 1 is merely one example of a therapy system that is configured to determine a patient state based on activity of a bioelectrical brain signal of patient 12 in one or more frequency sub-bands of a frequency band. Systems with other configurations of leads, electrodes, and sensors are possible. For example, in other implementations, IMD 16 may be coupled to additional leads or lead segments having one or more electrodes positioned at different target tissue sites, which may be within brain 28 or outside of brain (e.g., proximate to a spinal cord of patient 12, a peripheral nerve of patient 12, a muscle of patient 12, or any other suitable therapy delivery site). The additional leads may be used for delivering different stimulation therapies to respective stimulation sites within patient 12 or for monitoring at least one physiological parameter of patient 12.

Additionally, in other examples, a system may include more than one IMD. For example, a system may include two IMDs coupled to respective one or more leads. Each IMD can deliver stimulation to a respective lateral side of patient 12 in some examples.

As another example configuration, a therapy system can include one or more leadless electrical stimulators (e.g., microstimulators having a smaller form factor than IMD 16 and may not be coupled to any separate leads). The leadless electrical stimulators can be configured to generate and deliver electrical stimulation therapy to patient 12 via one or more electrodes on an outer housing of the electrical stimu-lator. In examples including a plurality of leadless electrical stimulators, the leadless electrical stimulators can be implanted at different target tissue sites within patient 12. One electrical stimulator may act as a "master" module that coordinates the delivery of stimulation to patient 12 via the plurality of electrical stimulators.

In some examples, IMD 16 is not configured to delivery electrical stimulation therapy to brain of patient 12, but, rather, is only configured to sense one or more physiological parameters of patient 12, including a bioelectrical brain signal of patient 12. This type of IMD 16 may a patient monitoring device useful for diagnosing patient 12, moni-toring a patient condition 12, or to train IMD 16 or another IMD for therapy delivery.

IMD 16 and/or external programmer 150 may receive information from one or more velocity sensors 160, e.g., directly via wireless communication or indirectly from an intermediate server via a network connection. Velocity sen-sor 160 may be positioned to sense velocity at a selected location on patient 105. In some examples, a velocity sensor 160 may be attached to a patient. In some examples, a velocity sensor 160 may be attached to an appendage of the patient 105 to sense the velocity associated with the append-age, e.g., by a clip-on mechanism, strap, elastic band and/or adhesive. In some examples, velocity sensor 160 (or one of a plurality of velocity sensors) may be implantable within patient 105, e.g., within the IMD 16. In some examples, a velocity sensor 160 may be unattached to a patient. For example, the velocity sensor 160 may be remote from a patient and scans the patient, such as, but not limited to video or a laser sensor. Examples of velocity sensor 160 include, but are not necessarily limited to, implants, watches, phones (e.g., with integrated pressure sensor or accelerometer, etc.), distance/range finders, pedometers, pother body worn devices (e.g., with accelerometers, gyro-scopes, pressure sensor, etc), devices that are stationary and the subject walks toward and away from the stationary device capturing velocity changes.

The velocity sensor 160 measures ambulatory velocity of a patient and provides information related to velocity at which the patient is able to walk, for example. For example, the velocity sensor 160 may provide a representation of velocity value, or other information indicative of velocity values or changes in velocity values, for the patient. The velocity value may be an instantaneous velocity measure-ment, or may be a measurement of velocity over a period of time such as average velocity value, maximum velocity value, minimum velocity value during the period of time. The IMD 16 provides therapy using stimulation having a particular set of stimulation parameters, and the programmer 150 may be used to modify the stimulation parameters for delivery of the stimulation. Using the information related to the velocity associated with the patient, for example velocity values, the particular stimulation parameters for therapy delivered by the IMD 16 may be selected or adjusted.

The velocity sensor 160 may be used to determine whether a velocity value or range of velocity values has been achieved for a set of stimulation parameters of the IMD. For example, one or more processors of velocity sensor 160, programmer 150 or IMD 16 may be configured to determine whether electrical stimulation with a particular set of stimu-lation parameters resulted in a sensed velocity value or change in sensed velocity value that was above a predeter-mined level, below a predetermined level, within a range prescribed by upper and lower levels, and/or increased from a previously sensed velocity. In some examples, the velocity sensor 160 may send raw velocity information or a change in velocity values to the external programmer 150, and the programmer 150 displays the raw velocity information or change in velocity values. The velocity values may be reviewed manually by a clinician or automatically evaluated by one or more processors of velocity sensor 160, external programmer 150 and/or IMD 16, or other remote processors via network connection.

Evaluation of the velocity value, including changes in velocity value or velocity value as compared to levels, ranges, or a matrix of predetermined velocity values as compared to a base line velocity value, in conjunction with the stimulation parameters, may indicate efficacy of stimu-lation parameters, such as the way the stimulation is deliv-ered (e.g., by selection of different amplitude, pulse width, pulse rate, and/or duty cycle). If the desired velocity value or change in velocity value is not detected, the programmer 150 can be used, for example via a user interface, to change the stimulation parameters, and the revised stimulation parameters may be objectively evaluated by reviewing the velocity values obtained while the IMD 16 provides stimu-lation using the revised stimulation parameters. The stimu-lation parameters may be manually changed for example in a clinical setting, e.g., via external programmer 150, remotely by a clinician, e.g., via a web browser client or application running on a remote computer, or automatically changed in a closed loop system, e.g., by external program-mer 150 or IMD 16. The revised stimulation parameters may be evaluated as producing either an improvement or decrease of the effectiveness of the stimulation therapy using the velocity values. By setting and adjusting stimulation parameters including electrode location using the velocity information, the system 100 and IMD 16 may be configured to deliver objectively efficacious therapy results for one or more diseases or disorders, such as DBS, painful diabetic neuropathy (PDN), peripheral vascular disease (PVD), peripheral artery disease (PAD), complex regional pain syndrome (CRPS), angina pectoris (AP), leg pain, back pain or pelvic pain.

Figure 2:
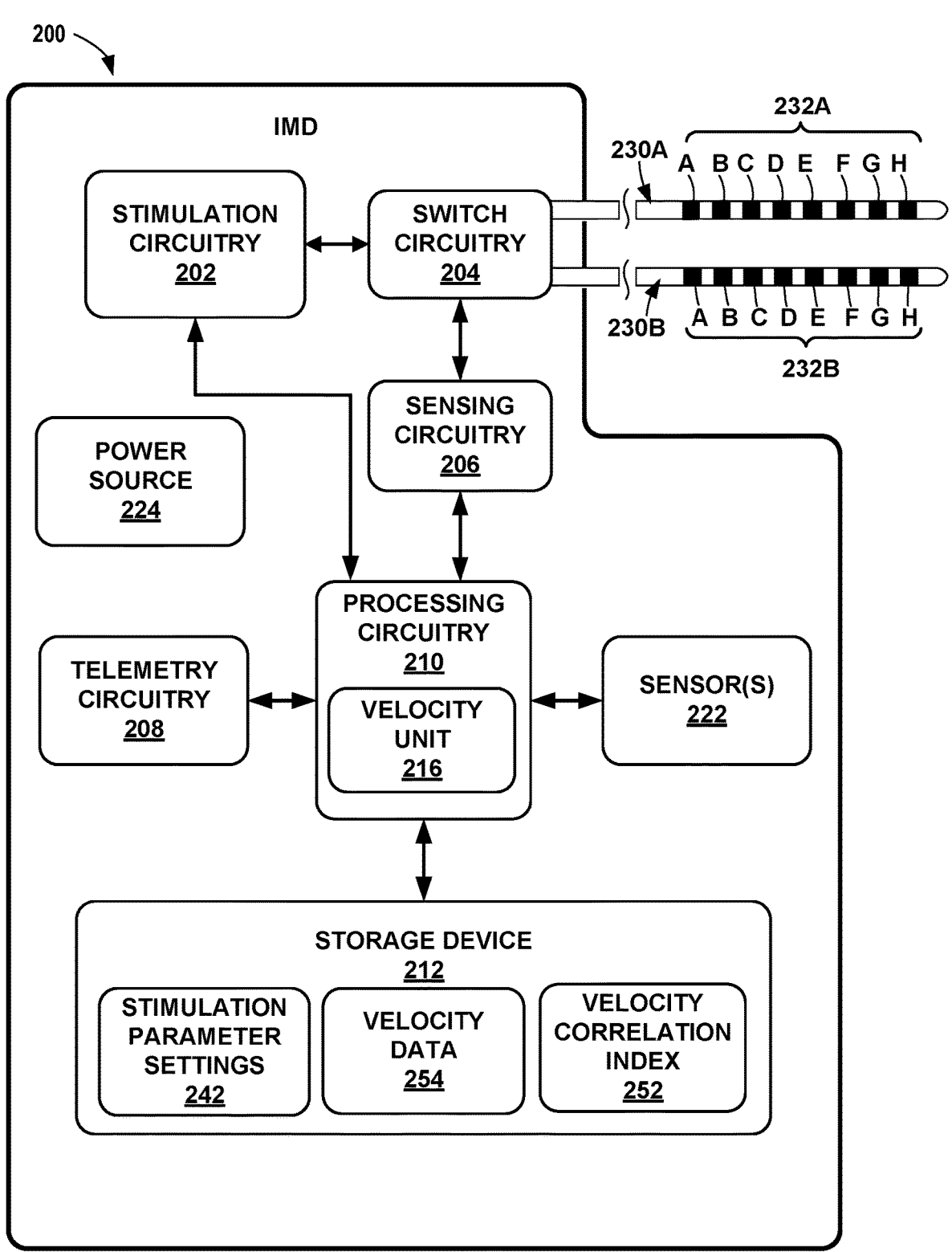
FIG. 2 is a block diagram illustrating an example of an IMD in the form of a brain stimulation device, in accordance with one or more techniques of this disclosure.

FIG. 2 is a functional block diagram illustrating example configurations of components of an IMD 200, in accordance with one or more techniques of this disclosure. IMD 200 may be an example of IMD 16 of FIG. 1. IMD 200 includes stimulation generation circuitry 202, switch circuitry 204, sensing circuitry 206, telemetry circuitry 208, processing circuitry 210, storage device 212, sensor(s) 222, power source 224, lead 230A carrying electrodes 232A, which may correspond to lead 20A and electrodes 24 of FIG. 1, and lead 230B carrying electrodes 232B, which may correspond to lead 20B and electrodes 26 of FIG. 1. Processing circuitry 210 may include one or more processors configured to perform various operations of IMD 200.

In the examples shown in FIG. 2, storage device 212 stores stimulation parameter settings 242. In addition, stor-age device 212 may store velocity data 254 obtained directly or indirectly from one or more velocity sensors 160 (FIG. 1), and a velocity correlation index 252 that defines correlations between velocity information and parameter information for delivery of electrical stimulation for stimulation, e.g., by indexing stimulation parameters or parameter adjustments to velocity value indicating velocity values or changes in velocity value. In some examples, IMD 200 of FIG. 2 may process sensed velocity information and select or adjust stimulation parameter settings based on the velocity information, or the processor circuitry of the IMD 200 automatically adjusts one or more of the stimulation parameters based on the relationship defined by the correlation index. In one or more examples, the parameter information may include one or more electrical stimulation parameters or parameter adjustments. In some examples, the velocity information includes a differential between multiple sensed velocity values, i.e., a first sensed ambulatory velocity and a subsequent sensed ambulatory velocity, and the parameter information includes electrical stimulation parameter adjustments.

In one or more examples, the IMD 200 does not store or receive the sensed velocity information. Instead, external programmer 150 or another device may directly or indirectly select or adjust stimulation parameter settings based on sensed velocity information and communicate the selected settings or adjustments to IMD 200 of FIG. 2. In some examples, stimulation parameter settings 242 may include stimulation parameters for respective different stimulation programs selectable by the clinician or patient for therapy. In some examples, stimulation parameter settings 242 may include one or more recommended parameter settings. In this manner, each stored therapy stimulation program, or set of stimulation parameters, of stimulation parameter settings 242 defines values for a set of electrical stimulation parameters (e.g., a stimulation parameter set), such as electrode combination (selected electrodes and polarities), stimulation current or voltage amplitude, stimulation pulse width, pulse rate, or duty cycle. In some examples, stimulation parameter settings 242 may further include cycling information indicating when or how long stimulation is turned on and off, (i.e., duty cycling). For example, recommended parameter settings may indicate the stimulation to turn on for a certain period of time, and/or to turn off stimulation for a certain period of time. In another example, recommended duty cycle parameter settings may indicate stimulation to turn on for a period of time without creating desensitization of the stimulation. In one or more examples, the recommended parameter settings may indicate stimulation to occur at a certain time of day, for example when the patient is typically awake or active, or sleeping. In one or more examples, recommended parameter settings relate to when the patient has a certain posture, for example when the patient is in a supine position.

Stimulation generation circuitry 202 includes electrical stimulation circuitry configured to generate electrical stimulation and generates electrical stimulation pulses selected to alleviate symptoms of one or more diseases, disorders or syndromes. While stimulation pulses are described, stimulation signals may take other forms, such as continuous-time signals (e.g., sine waves) or the like. The electrical stimulation circuitry may reside in an implantable housing, for example of the IMD. Each of leads 230A, 230B may include any number of electrodes 232A, 232B. The electrodes are configured to deliver the electrical stimulation to the patient.

Switch circuitry 204 may include one or more switch arrays, one or more multiplexers, one or more switches (e.g., a switch matrix or other collection of switches), or other electrical circuitry configured to direct stimulation signals from stimulation generation circuitry 202 to one or more of electrodes 232A, 232B, or directed sensed signals from one or more of electrodes 232A, 232B to sensing circuitry 206. In some examples, each of the electrodes 232A, 232B may be associated with respective regulated current source and sink circuitry to selectively and independently configure the electrode to be a regulated cathode or anode. Stimulation generation circuitry 202 and/or sensing circuitry 206 also may include sensing circuitry to direct electrical signals sensed at one or more of electrodes 232A, 232B.

Sensing circuitry 206 may be configured to monitor signals from any combination of electrodes 232A, 232B. In some examples, sensing circuitry 206 includes one or more amplifiers, filters, and analog-to-digital converters. Sensing circuitry 206 may be used to sense physiological signals, such as evoked compound action potential (ECAP) signals. In some examples, sensing circuitry 206 detects ECAP signals from a particular combination of electrodes 232A, 232B. In some cases, the particular combination of electrodes for sensing ECAP signals includes different electrodes than a set of electrodes 232A, 232B used to deliver stimulation pulses. Alternatively, in other cases, the particular combination of electrodes used for sensing ECAP signals includes at least one of the same electrodes as a set of electrodes used to deliver stimulation pulses to patient 105. Sensing circuitry 206 may provide signals to an analog-to-digital converter, for conversion into a digital signal for processing, analysis, storage, or output by processing circuitry 210.

Telemetry circuitry 208 supports wireless communication between IMD 200 and an external programmer, velocity sensing system, or another computing device under the control of processing circuitry 210. Processing circuitry 210 of IMD 200 may receive, as updates to programs, values for various stimulation parameters such as amplitude and electrode combination, from the external programmer via telemetry circuitry 208. Processing circuitry 210 may store updates to the stimulation parameter settings 242 or any other data in storage device 212. Telemetry circuitry 208 in IMD 200, as well as telemetry circuits in other devices and systems described herein, such as the external programmer and velocity sensing system, may accomplish communication by radiofrequency (RF) communication techniques. In addition, telemetry circuitry 208 may communicate with an external medical device programmer via proximal inductive interaction of IMD 200 with the external programmer, where the external programmer may be one example of external programmer 150 of FIG. 1. Accordingly, telemetry circuitry 208 may send information to the external programmer or the velocity sensing system on a continuous basis, at periodic intervals, or upon request from IMD 16 or the external programmer.

Processing circuitry 210 may include one or more processors, such as any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 210 herein may be embodied as firmware, hardware, software or any combination thereof. Processing circuitry 210 controls stimulation generation circuitry 202 to generate stimulation signals according to stimulation parameter settings 242. In some examples, processing circuitry 210 may execute other instructions stored in storage device 212 to apply stimulation parameters specified by one or more of programs, such as amplitude, pulse width, pulse rate, and pulse shape of each of the stimulation signals.

In the illustrated example of FIG. 2, processing circuitry 210 includes a velocity unit 216 to process the velocity information. Velocity unit 216 may represent an example of a portion of processing circuitry configured to process velocity information received from a velocity sensor, such as velocity sensor 160. In some examples, the processing of velocity information occurs in a device other than IMD 200. Referring again to FIG. 2, the velocity unit 216, discussed further below, receives information regarding the velocity data, such as information relating to sensed velocity associated with the patient 105, and controls the electrical stimulation circuitry 202 to deliver the electrical stimulation to the patient based on the received information, where the indications of the received information may be stored in a storage device. Velocity unit 216 may select or adjust electrical stimulation parameter settings in response to sensed velocity, e.g., to maintain velocity within, or drive velocity into, a desired range, or above a predetermined level, or below a predetermined level, where the range or level may be selected to promote beneficial levels of velocity to alleviate, reduce or delay onset of symptoms of diseases or disorders, or delay onset of damage or degeneration of tissue. In one example, IMD 200 delivers stimulation to a patient, for instance in a brain of a patient, with one or more parameter settings selected or adjusted based on sensed velocity of a patient. Processing circuitry 210 also controls stimulation generation circuitry 202 to generate and apply the stimulation signals to selected combinations of electrodes 232A, 232B. In some examples, stimulation generation circuitry 202 includes a switch circuit (instead of, or in addition to, switch circuitry 204) that may couple stimulation signals to selected conductors within leads 230, which, in turn, deliver the stimulation signals across selected electrodes 232A, 232B.

In some examples, velocity unit 216 of processing circuitry 210 may adjust one or more stimulation parameters based on sensed velocity of a patient. For example, the processing circuitry 210 may receive a first ambulatory velocity information of a patient while electrical stimulation with a first set of stimulation parameters is being delivered to the patient. The processing circuitry 210 may adjust, based on the first ambulatory velocity information and by a predetermined amount, one or more of the first set of stimulation parameters to generate an adjusted set of stimulation parameters by a predetermined amount. In some examples, the processing circuitry may receive a subsequent ambulatory velocity information of the patient while the electrical stimulation with an adjusted set of stimulation parameters is being delivered to the patient. In some examples, the processing circuitry may generate one or more recommended electrical stimulation parameters the patient based on the subsequent ambulatory velocity.

In some examples, adjusting the one or more of the first set of stimulation parameters by a predetermined amount may include adjusting the one or more of the first set of stimulation parameters at a first rate until the subsequent ambulatory velocity is greater than the first ambulatory velocity. In one or more examples, adjusting at the first rate may include increasing amplitude 0.1 mA per 0.5 sec. In one or more examples, adjusting the one or more of the first set of stimulation parameters by a predetermined amount may include adjusting the one or more of the first set of stimulation parameters at a second rate until the subsequent ambulatory velocity is less than or equal to the first ambulatory velocity. In some examples, the second rate includes increasing amplitude 0.1 per second.

Storage device 212 may be configured to store information within IMD 200 during operation. Storage device 212 may include a computer-readable storage medium or computer-readable storage device. In some examples, storage device 212 includes one or more of a short-term memory or a long-term memory. Storage device 212 may include, for example, random access memories (RAM), dynamic random access memories (DRAM), static random access memories (SRAM), magnetic discs, optical discs, flash memories, or forms of electrically programmable memories (EPROM) or electrically erasable and programmable memories (EEPROM). In some examples, storage device 212 is used to store data indicative of instructions, e.g., for execution by processing circuitry 210. As discussed above, storage device 212 is configured to store stimulation parameter settings 242.

Power source 224 is configured to deliver operating power to the components of IMD 200. Power source 224 may include a battery and a power generation circuit to produce the operating power. In some examples, the battery is rechargeable to allow extended operation. In some examples, recharging is accomplished through proximal inductive interaction between an external charger and an inductive charging coil within IMD 200. Power source 224 may include any one or more of a plurality of different battery types, such as nickel cadmium batteries and lithium ion batteries.

In some examples as shown in FIG. 2, the processing circuitry 210 of the IMD 200 directs delivery of electrical stimulation by the electrodes 232A, 232B of leads 230A, 230B, receives information relating to velocity from the velocity sensor, and generates output based on the received information. In some examples, receiving information relating to velocity may include receiving the first ambulatory velocity or the subsequent ambulatory velocity that may include sensing the ambulatory velocity of the patient with a velocity sensing device a sensor attached to the patient, and in some examples the sensor may be internal to the patient, such as within IMD. In some examples, receiving information relating to velocity may include receiving the first ambulatory velocity or the subsequent ambulatory velocity that may include sensing the ambulatory velocity of the patient with a velocity sensing device a sensor unattached to the patient.

The velocity unit 216 may use velocity information to develop efficacy indications or recommended electrical stimulation parameters or adjustments which are outputted to a user, where the user can use the indications or one or more recommended stimulation parameters to program the IMD 200, e.g., by selecting or accepting the recommendations as stimulation parameter settings to be used by IMD 200. For example, a particular electrode combination is recommended to a user and/or a set of stimulation parameters are recommended to a user and presented to the user via the programmer. The user may accept the recommended electrode combination and/or one or more recommended stimulation parameters, and the programmer programs IMD 200 to implement and deliver stimulation with the selected electrode combination and/or stimulation parameters. The user may pause, change, turn off, or restart velocity sensing and/or stimulation parameter recommendations.

In some examples, efficacy may be determined by delivering electrical stimulation with differing combinations of stimulation parameters, and monitoring sensed velocity and changes in sensed velocity as a result of delivery of electrical stimulation according to the differing stimulation parameters. The stimulation parameters may include, but are not limited to, electrode combination (e.g., selected electrodes and polarities), stimulation amplitude, stimulation pulse width, stimulation frequency, or duty cycle. Changes in velocity value may be changes from a measured baseline velocity value when stimulation was not delivered, or a previous velocity value when stimulation was delivered with particular stimulation parameters.

Processing circuitry 210 may control stimulation circuitry 202 to deliver stimulation energy with stimulation parameters specified by one or more stimulation parameter settings 242 stored on storage device 212 and to collect velocity information pertaining to the stored stimulation parameter settings 242. Processing circuitry 210 may collect this velocity information by receiving the information via telemetry from a remote velocity sensor at a remote site. Other options for the IMD 200 include the processing circuitry 210 collecting the velocity information from an onboard sensor, such as sensing velocity using the IMD. Processing circuitry 210 may also control stimulation circuitry 202 to test different parameter settings and record corresponding velocity values for each selected combination, and test different parameter settings as they compare to sensed velocity. For example, processing circuitry 210 directs stimulation circuitry 202 to deliver stimulation with a particular amplitude (and other parameter settings) and the velocity unit 216 collects the corresponding velocity value from telemetry circuitry 208. The velocity data 254 for this test may be stored in the storage device 212. Processing circuitry 210 may adjust the previously tested amplitude value of the stimulation delivered via the electrode combination to a different value by a predetermined amount and collect the corresponding velocity value from the velocity sensor in response to stimulation with the adjusted amplitude. The velocity value received for the stimulation at the changed stimulation parameter, in this example, amplitude, would be saved in the storage device 212 and may be output to a user. The processing circuitry 210 may continue to shift the amplitude values by either increasing or decreasing the amplitude, and recording the respective velocity values, which are stored on the storage device 212 and the information may be output to a user. While the example of amplitude is provided, processing circuitry 210 may direct stimulation circuitry 202 to step through various incremental settings of other stimulation parameters, such as stimulation pulse width, stimulation frequency, or duty cycle, and record the respective velocity information for each stepped value. In one or more examples, processing circuitry 210 may direct stimulation circuitry to turn on for a certain period of time, and/or to turn off for a period of time, or to turn on at a certain time of day and record the respective velocity value. In one example, the processing circuitry 210 cycles stimulation to turn on for 12 hours, and turn off for 12 hours. Stimulation circuitry 202 may shift more than one stimulation parameter for each test and collect sensed velocity information for each of the multiple shifted stimulation parameters.

Velocity unit 216 processes the collected sensed velocity information. In some examples, velocity unit 216 communicates the velocity information to a user and is configured to output the velocity information, where the output includes one or more velocity values. The user can use the velocity information to determine efficacy of a particular stimulation parameter setting, or a group of stimulation parameters, or track trends in velocity changes over time, e.g., with and without electrical stimulation, or with different parameter settings.

In some examples, the velocity unit 216 processes the information to perform closed loop control of the stimulation parameters based on the velocity information. The velocity unit 216 may store the velocity data 254 in storage device 212, and may interact with and/or develop a velocity correlation index to automatically adjust stimulation parameter settings 242 based on the velocity information. For example, velocity unit 216 may select or adjust one or more settings of parameter values, such as electrode combination, amplitude, pulse width or pulse rate, in response to sensed velocity information. The velocity information may be sensed when electrical stimulation is not delivered or upon delivery of electrical stimulation. In either case, velocity unit 216 may be configured to direct or control stimulation circuitry 202 to select or adjust one or more settings of parameter values to cause the sensed velocity to be above a predetermined level, below a predetermined level, or within a desired range of velocity values known or expected to be beneficial to patient 105.

Processing circuitry 210 may also control stimulation circuitry 202 to deliver, for each electrode combination, stimulation with different stimulation parameter combinations (e.g., amplitude, pulse width pulse rate, and/or duty cycle) and the sensed velocity value is recorded for the particular electrode combination and stimulation parameter combination. The changes in electrode combinations and/or parameter combinations may be manually changed by a user, or processing circuitry 210 may automatically test the various electrode pairs to, in effect scan through different positions and stimulation parameters of the electrical stimulation, and record the corresponding velocity information.

The velocity unit 216 may use the velocity data 254 to interact with and/or develop a velocity correlation index 252. The velocity correlation index 252 may include a matrix of information that tracks a relationship between two or more variables. For example, a first set of stimulation parameters (e.g., electrode combination, amplitude, pulse width, pulse rate, and/or duty cycle) may result in a first velocity value, and a second set of stimulation parameters may result in a second velocity value. In one or more examples, a third set of stimulation parameters may result in a third velocity value.

The first and second velocity values, and optionally the third velocity value, achieved using the first, second and third set of stimulation parameters may be further categorized within the velocity correlation index 252 by additional factors such as factors dependent on the patient condition, such as patient activity level, sensed patient temperature, sensed patient heart rate, patient diet input, patient pain input, patient sensitivity input, and/or other input from patient sensors. Additional factors can include factors independent of the patient including time of day, temperature, or increments of time. The correlation index 252 may include a log of velocity over time, and also after stimulation parameter settings have been adjusted. In one or more examples, the correlation index may include an input of a target velocity value or target velocity value change to be achieved, and as output a set of stimulation parameters or adjustments to produce the target velocity or target velocity change.

The velocity unit 216 may use the velocity data 254 with or without the velocity correlation index to inform a user of recommended parameter settings or automatically adjust stimulation parameter settings 242 using the IMD 200. For example, the IMD 200 may incrementally adjust stimulation parameters up or down in fixed increments until a target velocity value is achieved. Again, selected or adjusted stimulation parameter settings 242 may include electrode combinations (and hence location of stimulation), stimulation amplitude, stimulation pulse width, stimulation pulse rate, and/or duty cycle, and may further include consideration of patient activity level, patient posture, sensed glucose level, patient diet input, patient pain input, patient sensitivity input, other input from patient sensors, patient temperature, external temperature, and/or time of day. The velocity unit 216 receives the velocity data 254, and the velocity unit 216 processes the data to determine if stimulation should be adjusted, for example, if the velocity data 254 falls below a threshold velocity value, increases beyond an upper limit for velocity value, or falls outside of a range of values. In an example, velocity unit 216 may select stimulation parameters or apply a prescribed adjustment to stimulation parameters. If velocity unit 216 determines the stimulation parameters should be changed based on the current or trending velocity values, the velocity unit 216 may automatically implement a change in one or more stimulation parameter settings and record the revised velocity data for the adjusted stimulation parameter settings, or velocity unit 216 may recommend a change in parameter settings to a user, for example by communication to an external controller. If the implemented changes in the one or more stimulation parameters settings do not achieve an expected or desired velocity, the stimulation parameter settings may be changed, and the velocity value is evaluated again. This process may be repeated until the desired velocity value is achieved or until increases in ambulatory velocity are no longer achieved.

Figure 3:
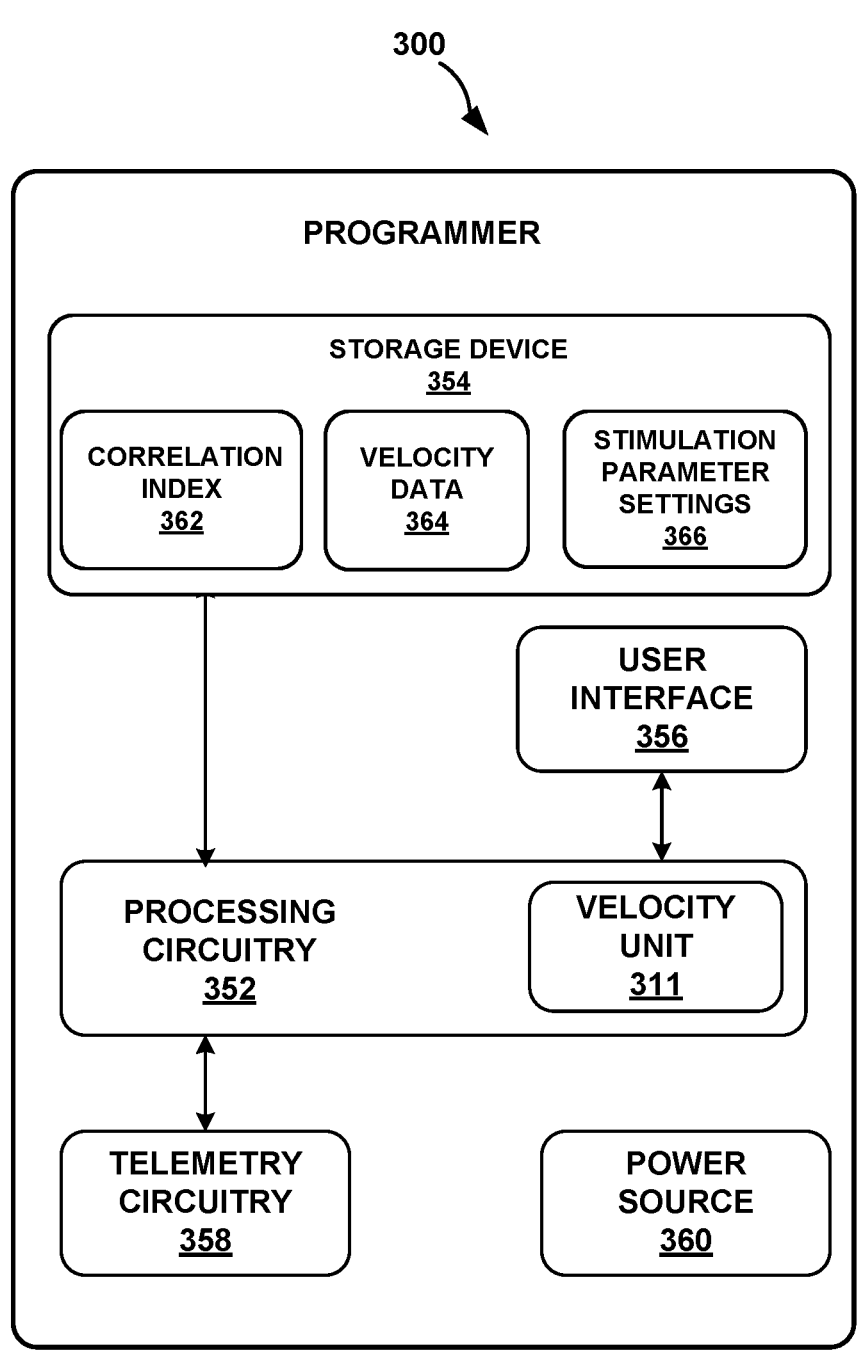
FIG. 3 is a block diagram illustrating an example of an external programmer suitable for use with the IMD of FIG. 2, in accordance with one or more techniques of this disclosure.

FIG. 3 is a block diagram illustrating an example configuration of components of an example external programmer 300. External programmer 300 may be an example of external programmer 150 of FIG. 1. Although external programmer 300 may generally be described as a hand-held device, such as a tablet computer or smartphone-like device, external programmer 300 may be a larger portable device, such as a laptop computer, or a more stationary device, such as a desktop computer. In addition, in other examples, external programmer 300 may be included as part of an external charging device or include the functionality of an external charging device, e.g., to recharge a battery or batteries associated with IMD 200. As illustrated in FIG. 3, external programmer 300 may include processing circuitry 352, storage device 354, user interface 356, telemetry circuitry 358, and power source 360. In some examples, storage device 354 may store instructions that, when executed by processing circuitry 352, cause processing circuitry 352 and external programmer 300 to provide the functionality ascribed to external programmer 300 throughout this disclosure. Each of these components, circuitry, or modules, may include electrical circuitry that is configured to perform some, or all of the functionality described herein. For example, processing circuitry 352 may include processing circuitry configured to perform the processes discussed with respect to processing circuitry 352.

In general, external programmer 300 includes any suitable arrangement of hardware, alone or in combination with software and/or firmware, to perform the techniques attributed to external programmer 300, and processing circuitry 352, user interface 356, and telemetry circuitry 358 of external programmer 300. In various examples, processing circuitry 352, telemetry circuitry 358, or other circuitry of external programmer 300 may include one or more processors, such as one or more microprocessors, DSPs, ASICs, FPGAs, or any other equivalent integrated or discrete logic circuitry, as well as any combinations of such components. External programmer 300 also, in various examples, may include a storage device 354, such as RAM, ROM, PROM, EPROM, EEPROM, flash memory, a hard disk, a CD-ROM, including executable instructions for causing the one or more processors to perform the actions attributed to them. Moreover, although processing circuitry 352 and telemetry circuitry 358 are described as separate modules, in some examples, processing circuitry 352 and telemetry circuitry 358 are functionally integrated. In some examples, processing circuitry 352, telemetry circuitry 358 or other circuitry of external programmer 300 may correspond to individual hardware units, such as ASICs, DSPs, FPGAs, or other hardware units.

The processing circuitry 352 is configured to direct delivery of electrical stimulation, receive information relating to patient ambulatory velocity upon the delivery of the electrical stimulation, and generate as at least part of the output based on the received information, e.g., for evaluation of efficacy of stimulation parameters and/or recommend, or assist a user in programming, stimulation parameters for delivery of electrical stimulation. In some examples, the processing circuitry 352 is configured to control the electrical stimulation circuitry to deliver the electrical stimulation based on the velocity information in a closed loop basis by directing the IMD to use particular stimulation parameters.

In some examples, velocity unit 311 of processing circuitry 352 may adjust one or more stimulation parameters based on sensed velocity of a patient. For example, the processing circuitry 352 may receive a first ambulatory velocity information of a patient while electrical stimulation with a first set of stimulation parameters is being delivered to the patient. The processing circuitry 352 may adjust, based on the first ambulatory velocity information and by a predetermined amount, one or more of the first set of stimulation parameters to generate an adjusted set of stimulation parameters by a predetermined amount. In some examples, the processing circuitry may receive a subsequent ambulatory velocity information of the patient while the electrical stimulation with an adjusted set of stimulation parameters is being delivered to the patient. In some examples, the processing circuitry may generate one or more recommended electrical stimulation parameters the patient based on the subsequent ambulatory velocity.

In some examples, adjusting the one or more of the first set of stimulation parameters by a predetermined amount may include adjusting the one or more of the first set of stimulation parameters at a first rate until the subsequent ambulatory velocity is greater than the first ambulatory velocity. In one or more examples, adjusting at the first rate may include increasing amplitude 0.1 mA per 0.5 sec. In one or more examples, adjusting the one or more of the first set of stimulation parameters by a predetermined amount may include adjusting the one or more of the first set of stimulation parameters at a second rate until the subsequent ambulatory velocity is less than or equal to the first ambulatory velocity. In some examples, the second rate includes increasing amplitude 0.1 per second. In one or more examples, a clinician may set a range of parameter values in which to measure the ambulatory velocity. For example, the clinician may set a starting amplitude value and an ending amplitude value, and the processor directs the stimulation to be delivered at the starting amplitude value and steps up in value until it reaches the ending amplitude value. As the processor directs the values to step through the amplitudes, patient velocity is measured for each value and stored. The processor may recommend parameter settings based on the measured patient velocity.

Storage device 354 (e.g., a storage device) may, in some examples, store instructions that, when executed by processing circuitry 352, cause processing circuitry 352 and external programmer 300 to provide the functionality ascribed to external programmer 300 throughout this disclosure. For example, storage device 354 may include instructions that cause processing circuitry 352 to obtain a parameter set from memory or receive user input and send a corresponding command to IMD 200, or instructions for any other functionality. In addition, storage device 354 may include a plurality of programs, where each program includes a parameter set that defines therapy stimulation or control stimulation. Storage device 354 may also store data received from a medical device (e.g., IMD 16) and/or a remote sensing device. For example, storage device 354 may store data recorded at a sensing module of the medical device, and storage device 354 may also store data from one or more sensors of the medical device. In an example, storage device 354 may store data recorded at a remote sensing device such as velocity values sensed from velocity sensors.

User interface 356 may include a button or keypad, lights, a speaker for voice commands, a display, such as a liquid crystal (LCD), light-emitting diode (LED), or organic light-emitting diode (OLED). In some examples, the display includes a touch screen. User interface 356 may be configured to display any information related to the delivery of electrical stimulation including output, for example, based on the velocity information. User interface 356 may also receive user input (e.g., indication of when the patient perceives stimulation, or a pain score perceived by the patient upon delivery of stimulation) via user interface 356. The user input may be, for example, in the form of pressing a button on a keypad or selecting an icon from a touch screen. The input may request starting or stopping electrical stimulation, the input may request a new electrode combination or a change to an existing electrode combination, or the input may request some other change to the delivery of electrical stimulation, such as a change in stimulation amplitude, pulse width or pulse rate.

Telemetry circuitry 358 may support wireless communication between the medical device and external programmer 300 under the control of processing circuitry 352. Telemetry circuitry 358 may also be configured to communicate with another computing device via wireless communication techniques, or direct communication through a wired connection. In some examples, telemetry circuitry 358 provides wireless communication via an RF or proximal inductive medium. In some examples, telemetry circuitry 358 includes an antenna, which may take on a variety of forms, such as an internal or external antenna.

Examples of local wireless communication techniques that may be employed to facilitate communication between external programmer 300 and IMD 16 include RF communication according to the 802.11 or Bluetooth® specification sets or other standard or proprietary telemetry protocols. In this manner, other external devices may be capable of communicating with external programmer 300 without needing to establish a secure wireless connection. As described herein, telemetry circuitry 358 may be configured to transmit a spatial electrode movement pattern or other stimulation parameters to IMD 16 for delivery of electrical stimulation therapy.

Power source 360 is configured to deliver operating power to the components of external programmer 300. Power source 360 may include a battery and a power generation circuit to produce the operating power. In some examples, the battery is rechargeable to allow extended operation. Recharging may be accomplished by electrically coupling power source 360 to a cradle or plug that is connected to an alternating current (AC) outlet. In addition, recharging may be accomplished through proximal inductive interaction between an external charger and an inductive charging coil within external programmer 300. In other examples, traditional batteries (e.g., nickel cadmium or lithium ion batteries) may be used. In addition, external programmer 300 may be directly coupled to an alternating current outlet to operate.

In some examples, the external programmer 300 or external control device directs delivery of electrical stimulation of an IMD, receives information relating to velocity with delivery of the electrical stimulation, and generates output based on the received information, e.g., for evaluation of efficacy of stimulation parameters and/or recommend, assist a user in programming, stimulation parameters for delivery of electrical stimulation, or used as part of a closed loop control device to automatically adjust stimulation parameters using velocity information. In one or more examples, the control device generates output based on a first received information and a second received information via a user interface device.

Programmer 300 may be a patient programmer or a clinician programmer and receives velocity information such as velocity data 364. Programmer 300 receives velocity information and allows a user to interact with the processing circuitry 352 via user interface 356 in order to identify efficacious parameter settings, such as electrode combinations and/or one or more other stimulation parameters using the velocity information. Programmer 300 further assists the user in programming a neurostimulation device by using the velocity information displayed on the user interface 356. In addition, programmer 300 may be used as part of a closed loop control device to automatically adjust stimulation parameters based at least on velocity information. In some examples, programmer 300 receives velocity information such as velocity data 364 from the velocity device and stores the velocity data in the storage device 354.

Programmer 300 may be used to determine efficacy of particular parameter settings of the IMD by testing parameter settings and recording velocity for each parameter setting. Information resulting from the testing may be presented to a user via the user interface 356. Programmer 300 may receive user input via the user interface device following generation of the output based on the first received information and the second received information, selecting one or more stimulation parameters for the delivery of the electrical stimulation. In one or more examples, the programmer 300 may generate a third set of stimulation parameters for delivery of the electrical stimulation based on the user input. In some examples, the programmer 300 compares the first information that was received relating to the first velocity with the second information relating to the second velocity, and automatically generates a third set of stimulation parameters for delivery of the electrical stimulation based on the comparison.

In an example, programmer 300 may be used to cause the IMD to automatically scan though a plurality of electrode combinations or parameter combinations. Processing circuitry 352 causes the IMD to automatically scan through each of a plurality of parameter combinations, including electrode combinations and parameter combinations. For each combination, the programmer 300 obtains and records the corresponding sensed velocity value.

Processing circuitry 352 controls stimulation circuitry 202 to deliver stimulation energy with stimulation parameters specified by one or more stimulation parameter settings 366 stored on storage device 354, and to collect velocity information pertaining to the stored stimulation parameter settings 366. Processing circuitry 352 may also control stimulation circuitry 202 to test different parameter settings and record corresponding velocity values for each selected combination, and test different parameter settings as they compare to sensed velocity. For example, processing circuitry 352 directs stimulation circuitry 202 to deliver stimulation with a particular amplitude and the velocity unit 311 collects the corresponding velocity value from telemetry circuitry 358. The velocity data 364 for this test may be stored in the storage device 354 and in the velocity correlation index 362, where the processing circuitry indexes the received velocity data to one or more stimulation parameters of the electrical stimulation.

Processing circuitry 352 may be configured to shift the previously tested amplitude value to a different value and collect the corresponding velocity value from the velocity sensor. The velocity value received for the stimulation at the changed stimulation parameter, in this example amplitude, would be saved in the storage device 354. The processing circuitry 352 may continue to shift the amplitude values by either increasing or decreasing the amplitude, and record the respective velocity values, which are stored on the storage device 354 and the information is output, e.g., via user interface 356. While the example of amplitude is provided, processing circuitry 352 may direct stimulation circuitry to step through various incremental settings of other stimulation parameters, such as stimulation pulse width, stimulation frequency, or duty cycle, and record the respective velocity information for each stepped value. Stimulation circuitry 202 may shift more than one stimulation parameter for each test and collect sensed velocity information for the multiple shifted stimulation parameters.

In some examples, the processing circuitry 352 of programmer 300 directs delivery of electrical stimulation of the electrodes 232A, 232B, and receives information relating to velocity from the velocity sensor, and controls the delivery of electrical stimulation of the electrodes 232A, 232B based on the received information in a closed loop setting. The velocity information may be received via the telemetry circuitry 358 either directly or indirectly from the velocity sensor 160 (FIG. 1). In an example, the controller receives the velocity information from an intermediate device other than velocity sensor 160.

The velocity unit 311 processes the velocity information. In some examples, the velocity unit 311 processes the information to perform closed loop control of the stimulation parameters based on the velocity information. The velocity unit 311 may store the velocity data 364 in storage device 354, and may interact with and/or develop a velocity correlation index to adjust stimulation parameter settings 366, for example automatically adjusting the stimulation parameter settings 366 based on the velocity correlation index.

In an example, the velocity unit 311 receives velocity data 364 to store in storage device 354. The velocity data 364 may be raw data from the velocity sensor 160 such as velocity, velocity change, rate of change of velocity, or processed data. The processed data may include raw data that has been evaluated and processed into other categories, such as a rating of high, medium, low. In some examples, the processed data relates to a numeric score, or a value rating.

The velocity unit 311 may use the velocity data 364 with or without the velocity correlation index to develop recommended parameter settings or automatically adjust stimulation parameter settings 366 using the programmer 300. The velocity unit 311 receives the velocity data 364, and the velocity unit 311 processes the data to determine if stimulation should be adjusted, for example if the velocity data 364 falls below a threshold velocity value, exceeds an upper limit value, or falls outside of a range of values. If velocity unit 311 determines the stimulation parameters should be changed based on the current or trending velocity values, the velocity unit 311 may automatically implement a change in one or more stimulation parameter settings and record the revised velocity data for the adjusted stimulation parameter settings, or velocity unit 311 may recommend a change in parameter settings to a user. The change in stimulation parameter settings may be developed using the velocity correlation index 362. If the implemented changes in the one or more stimulation parameters settings do not achieve an expected or desired velocity, the stimulation parameter settings may be changed, and the velocity value is evaluated again. This process may be repeated until the desired velocity value is achieved.

Programmer 300 presents to the user a list of the electrode combinations with associated velocity indications, or a list of combined electrode and parameter combinations with associated velocity indications so that the user can select one of them. Programmer 300 may also highlight recommended combinations based upon predetermined priorities such as maximizing velocity with best energy efficiency. For example, programmer 300 may highlight or otherwise identify sets of stimulation parameters (e.g., electrode combinations, electrode polarities, stimulation amplitude, stimulation pulse width, stimulation pulse rate, and/or duty cycle) that produce sensed velocity values that are closest to a predetermined target velocity value, above a predetermined velocity value, below a predetermined velocity value, or within a velocity value range. The sets of stimulation parameters may be sortable according to velocity value or proximity to a predetermined velocity value. As a further example, programmer 300 highlight or otherwise identify sets of stimulation parameters (e.g., electrode combinations, electrode polarities, stimulation amplitude, stimulation pulse width, stimulation pulse rate, and/or duty cycle) that produce sensed velocity values that are proximate to a predetermined velocity value, or within a predetermined velocity value range, and require less energy consumption to achieve such sensed velocity values, e.g., in terms of energy consumption associated with the stimulation intensity presented by stimulation amplitude, pulse width, pulse rate, and/or duty cycle. In this manner, programmer 300 may facilitate selection of sets of stimulation parameters that promote desired velocity values and reduce power consumption by IMD 200.

The provided output of sets of stimulation parameter values and resultant velocity indications may include raw velocity values, relative scores (1-x) for velocity, or rankings of the tested combinations according to best velocity (e.g., vs. a target velocity) and/or best velocity and energy efficiency.

The architecture of external programmer 300 illustrated in FIG. 3 is shown as an example. The techniques as set forth in this disclosure may be implemented in the example external programmer 300 of FIG. 3, as well as other types of systems not described specifically herein. Nothing in this disclosure should be construed so as to limit the techniques of this disclosure to the example architecture illustrated by FIG. 3.

Figure 4:
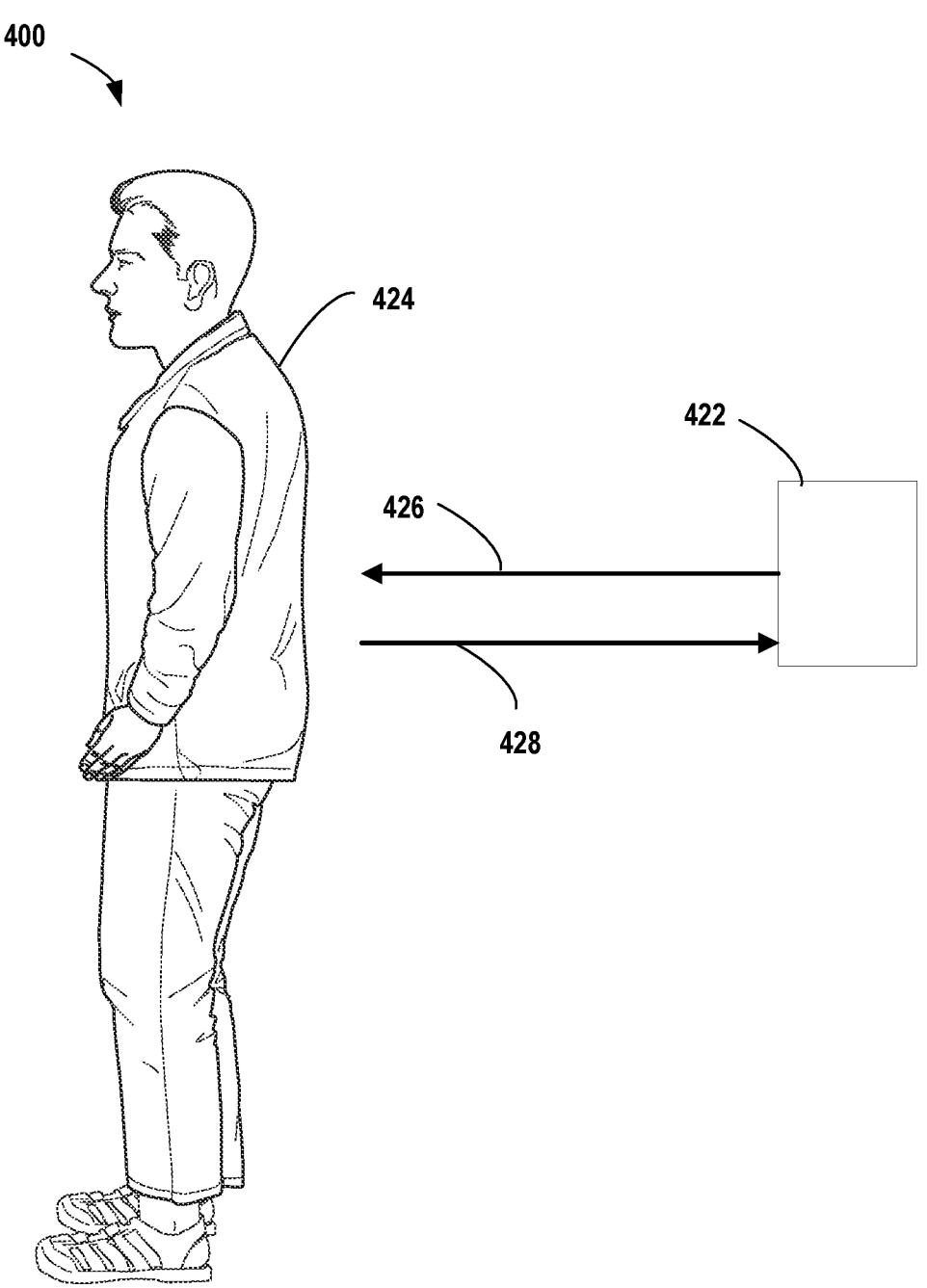
FIG. 4 is a block diagram illustrating an example of a velocity sensor suitable for use with the IMD of FIG. 2 and the programmer of FIG. 3, in accordance with one or more techniques of this disclosure.

FIG. 4 is an example of a velocity sensing system 400 suitable for use with the IMD of FIG. 2 and the programmer of FIG. 3, in accordance with one or more techniques of this disclosure. The velocity sensing system 400 allows for a determination of ambulatory velocity of a patient, for example using an unattached sensor using laser, doppler, or optical techniques.

In some examples, velocity sensing system 400 may include a velocity sensor that includes a source such as emitter configured to emit light, and a detector configured to detect at least a transmitted or reflected portion of the light emitted by the emitter/detector 422 that emits a signal 426 toward a patient, and detects a return signal 428 comes back from the patient. In some examples, the signal 426 may be directed to a trunk of a patient, which may allow for a clear interface of ambulatory velocity of the patient. In some examples, the signal 426 may be directed to the legs of a patient. In one or more examples, the signal 426 may be directed to a front of a patient, or a side of a patient to measure gait. In use, in some examples, processing circuitry directs emitter/receiver 422 to transmit a signal toward the patient. The system 400 may further include a receiver to detect the return signal from the patient to determine the ambulatory velocity of the patient.

Velocity sensing system 400 further includes sensor circuitry configured to generate information relating to velocity based on the detected portion of the signal. Velocity sensing system 400 may further include communication circuitry configured to transmit the velocity information to processing circuitry or the programmer, which processes the data and determines ambulatory velocity of the patient.

Telemetry circuitry may support wireless communication between the system 400 and the programmer 300 (FIG. 3). Telemetry circuitry of the system 400 may also be configured to communicate with another computing device via wireless communication techniques, or direct communication through a wired connection. In some examples, telemetry circuitry provides wireless communication via an RF or proximal inductive medium. In some examples, telemetry circuitry includes an antenna, which may take on a variety of forms, such as an internal or external antenna.

Figure 5:
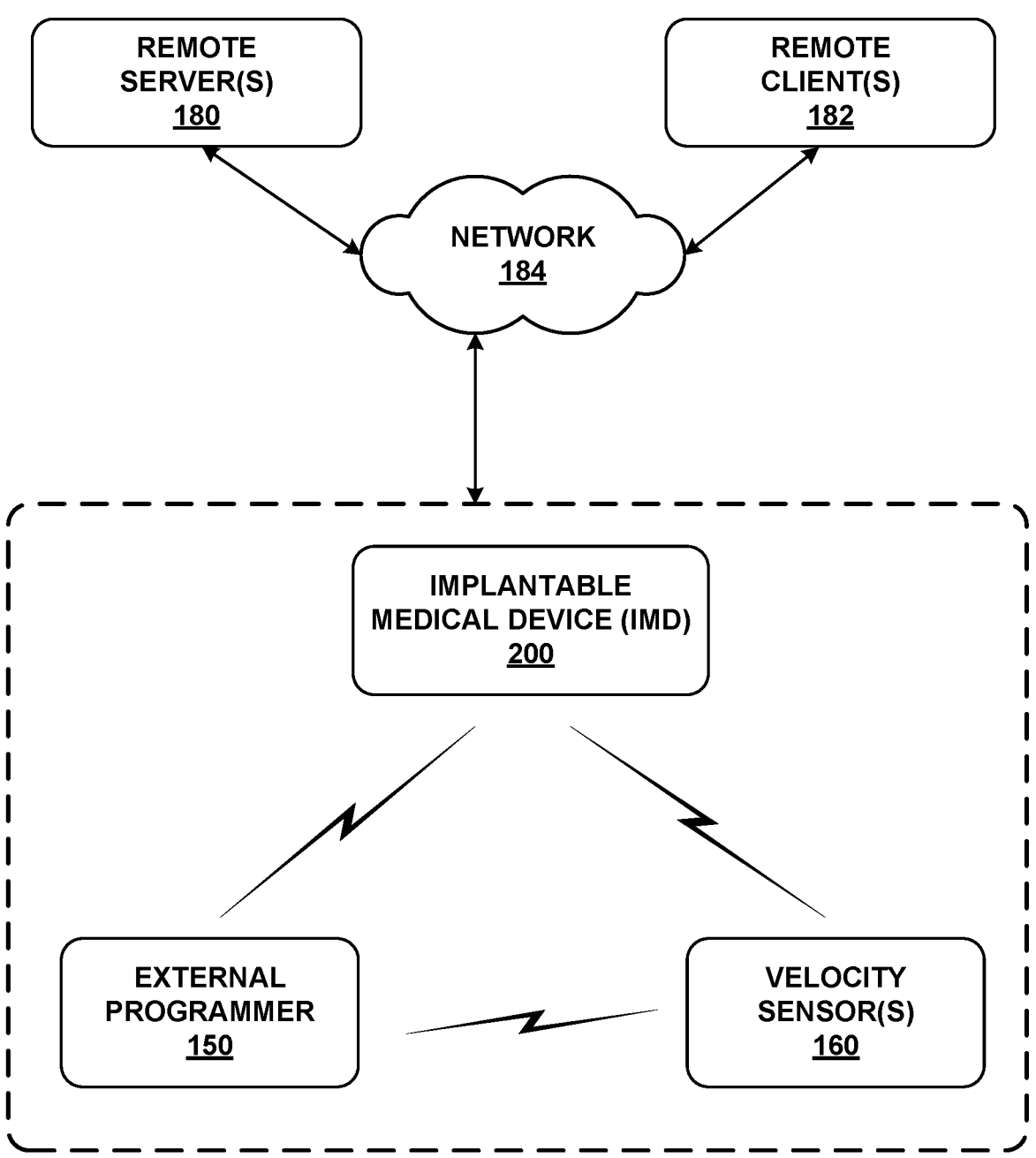
FIG. 5 is a user interface diagram of an external programmer or remote monitoring/programming device suitable for use in the system of FIG. 1.

FIG. 5 is a block diagram of a system for evaluating efficacy of, assisting a user in programming, and/or automatically controlling stimulation or stimulation parameters using the techniques disclosed herein, including the use of velocity information. In some examples, a remote system such as remote server 180 can receive parameter information and/or velocity information via network 184 and may process the velocity information, or may process the velocity information in combination with parameter information. In some examples, remote server 180 may store the parameter information and/or velocity information and process such information may be performed on a different remote server. The network 184 may comprise one or more wired and/or wireless networks. In some examples, network 184 may be the Internet.

In one or more examples, methods and use of the systems may be performed by a single device or among multiple devices located in separate locations. In an example, velocity information from the velocity sensor 160 and parameter information from the external programmer 150 or the implantable device is sent to the remote server 180 via the network 184. The remote server 180 may perform analysis over time on some or all of the received data to create correlation indices based on received data from a single patient or multiple patients. Remote server 180 processes the information to develop efficacy information, correlation indices, parameter recommendations, and communicates the processed information to the implantable stimulator or external programmer 150. In some examples, a clinician may view efficacy information, correlation indices, parameter recommendations via remote client 182 accessing remote server 180 and may program the IMD using the remote client 182 and the remote server 180. In some examples, the remote server 180 and may automatically program or control the IMD using the remote client 182 and the remote server 180 in closed loop control.

In one or more examples, a patient has a velocity sensing device at home which checks velocity persistently or intermittently over time, for instance at regular or irregular intervals. In one or more examples where a patient has a velocity sensing device at home which checks velocity persistently or intermittently, for example the IMD, the velocity sensing device may provide a notification of newly sensed velocity information via network 184 to a remote client 182. Remote client 182 may prompt a clinician to check the newly sensed velocity information and consider programming changes. The clinician may utilize a user interface of remote client 182 to review efficacy, enter stimulation parameter programming changes, and/or accept recommended stimulation parameter changes generated automatically by remote server 180. Remote server 180 can send the programming changes to the IMD 200 via network 184. In some examples, the remote server 180 may remotely retrieve velocity information from the IMD, programmer, or velocity sensing device, and may send programming directly to the IMD or to the IMD via the programmer. In some examples, the programmer, IMD, and/or velocity sensing device communicate with the remote server 180 over a network connection through a network access device.

Figure 6:
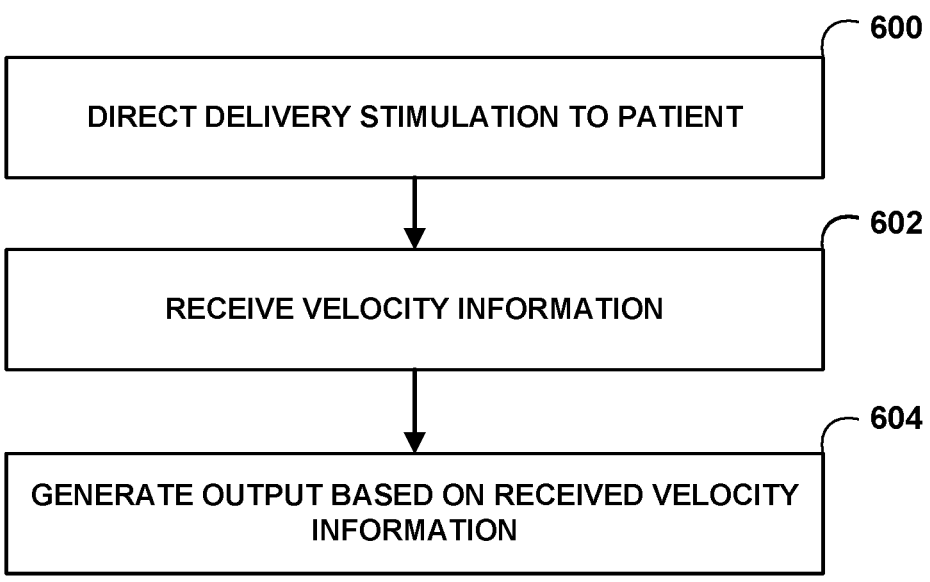
FIG. 6 is a flow diagram illustrating delivering stimulation while receiving sensed velocity information.

FIG. 6 is a flow diagram illustrating delivering electrical stimulation based on velocity information. In an example, one or more processors may be configured to direct electrical stimulation to a patient (600), for example via electrodes to deliver the electrical stimulation generated by electrical stimulation circuitry. In one or more examples, the one or more processors directly control electrical stimulation, or indirectly control electrical stimulation by generating an instruction for indirect control of the electrical stimulation.

At 602, the processors may receive information relating to ambulatory velocity associated with the patient upon the delivery of the electrical stimulation to the patient, such as velocity values. In one or more examples, the information may be collected with a velocity sensing device configured to sense the velocity associated with the patient. The velocity sensing device may include an external velocity sensor or an implantable velocity sensor. In some examples, the processor receives information relating to a first ambulatory velocity and/or a subsequent ambulatory velocity by sensing with a first sensor internal to the patient and by sensing with a second sensor unattached to the patient. In some examples, the processor correlates data of the first sensor with the second sensor. The received information may be sent and/or received from the velocity sensing device via wireless telemetry.

The processors may generate output based on the received information (604). In one or more examples, the output may include velocity values, and/or one or more electrical stimulation efficacy indications for the delivered electrical stimulation. In one or more examples, the output may include one or more recommended electrical stimulation parameters for the delivery of the electrical stimulation, such as one or more of electrode combination, stimulation amplitude, stimulation pulse width, stimulation frequency, or duty cycle. In one or more examples, the one or more processors may be configured to generate the output based on the received information via a user interface.

In one or more examples, the one or more processors may be configured to receive user input selecting one or more stimulation parameters or multiple sets of stimulation parameters of the electrical stimulation and direct delivery of the electrical stimulation based on the selected stimulation parameters or multiple sets of stimulation parameters, and optionally the output includes respective velocity values for each of the multiple sets of stimulation parameters, and/or electrical stimulation efficacy indications for the delivered electrical stimulation based on the respective velocity values for each of the multiple sets of stimulation parameters. In one or more examples, the one or more processors may be configured to store indications of the received information in association with the multiple sets of stimulation parameters. In one or more examples, the electrical stimulation includes one or more parameters selected to deliver therapy to address a condition of one or more of painful diabetic neuropathy (PDN), peripheral vascular disease (PVD), peripheral artery disease (PAD), complex regional pain syndrome (CRPS), angina pectoris (AP), leg pain, back pain or pelvic pain. The output may be used to develop recommended stimulation parameters, and be presented to a user (such as a clinician or patient) and/or automatically implemented.

Figure 7:
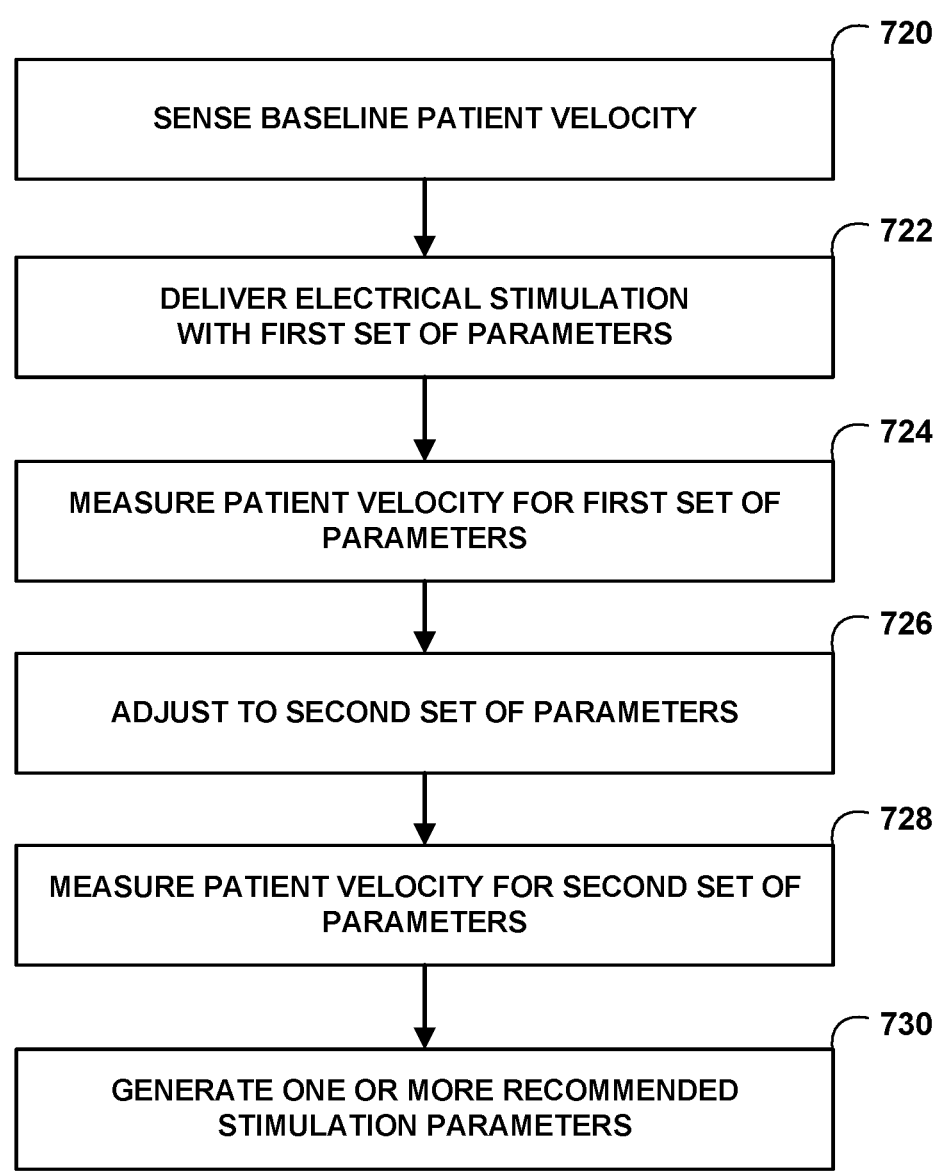
FIG. 7 is a flow diagram illustrating programming of one or more stimulation parameters based on sensed velocity information.

FIG. 7 is a flow diagram illustrating controlling electrical stimulation based on velocity information. In one or more examples, the system senses a baseline patient ambulatory velocity (720), with for example, a velocity sensing device attached to the patient or a device unattached to the patient. The baseline velocity may be measure without providing electrical stimulation. At (722), electrical stimulation circuitry may be configured to generate electrical stimulation to a patient, for example via electrodes to deliver the electrical stimulation generated by electrical stimulation circuitry with a first set of parameters. In one or more examples, one or more processors directly control electrical stimulation, or indirectly control electrical stimulation by generating an instruction for indirect control of the electrical stimulation. At 724, a patient ambulatory velocity is measured for the first set of parameters using the velocity sensors, for example, as mentioned above. The patient velocity may be compared to the baseline patient velocity. In one or more examples, the processing circuitry, which may include processors, may receive information relating to patient ambulatory velocity upon the delivery of the electrical stimulation to the patient, such as velocity values.

The processing circuitry may control the electrical stimulation circuitry adjust to a second set of parameters, for example by a predefined amount. (726). In one or more examples, the processing circuitry may be configured to adjust, by a predetermined amount, one or more of the stimulation parameters of the electrical stimulation if the received information indicates velocity value fails to increase from the baseline velocity, is outside a range of velocity values, is below a minimum velocity value, or exceeds a maximum velocity value. In some examples, adjusting the one or more of the first set of stimulation parameters by a predetermined amount may include adjusting the one or more of the first set of stimulation parameters at a first rate until the subsequent ambulatory velocity is greater than the first ambulatory velocity. In one or more examples, adjusting at the first rate may include increasing amplitude 0.1 mA per 0.5 sec. In one or more examples, adjusting the one or more of the first set of stimulation parameters by a predetermined amount may include adjusting the one or more of the first set of stimulation parameters at a second rate until the subsequent ambulatory velocity is less than or equal to the first ambulatory velocity. In some examples, the second rate includes increasing amplitude 0.1 per second.

The system measures the patient ambulatory velocity for the second or subsequent set of parameters (728). The processor evaluates the relative velocities and parameter settings and generates one or more recommended stimulation parameters based on the evaluation (730). In determining efficacy of the stimulation, the velocity information is correlated to the parameter settings, and evaluated relative to the parameter settings, where a degree of increased velocity typically indicates efficacy of the parameter setting. In some examples, the parameter settings may be ranked by velocity readings. By ranking the velocity readings, a list of stimulation parameters that produce a desired velocity may be developed, identifying particularly efficacious parameter settings. In one or more examples, ranking of the velocity readings from high to low and including ranges of acceptable velocity readings will determine efficacy of multiple parameter combinations such as, but not limited to stimulation amplitude, pulse width and pulse frequency. In one or more examples, velocity readings may be further ranked by patient information, such as by stimulation perception score, patient activity level, posture, time of day, and other input from patient sensors. The programmer may provide efficacy ratings for the various parameters to be viewed by a clinician, or the user can view velocity to evaluate the efficacy of the different settings.

In one or more examples, the processing circuitry may be configured to adjust one or more of the stimulation parameters of the electrical stimulation to achieve a desired velocity over a period of time. In one or more examples, the processing circuitry may be configured to adjust a duty cycle of the stimulation parameters of the electrical stimulation to achieve the desired velocity over a period of time to reduce desensitization to the stimulation. In one or more examples, the processing circuitry may be configured to further adjust and/or deliver stimulation conditional on patient information such as patient posture and/or other information such as time of day.

In one or more examples, the programmer will test one or more combinations of stimulation parameters, collecting and storing information relating to ambulatory velocity measured during stimulation at each of the parameter settings. The information relating to the measured velocity at each of the stimulation parameters is used to determine stimulation efficacy. Velocity may be automatically logged with each adjustment of parameters, the changes to velocity may be identified by plotting velocity over time.

Figure 8:
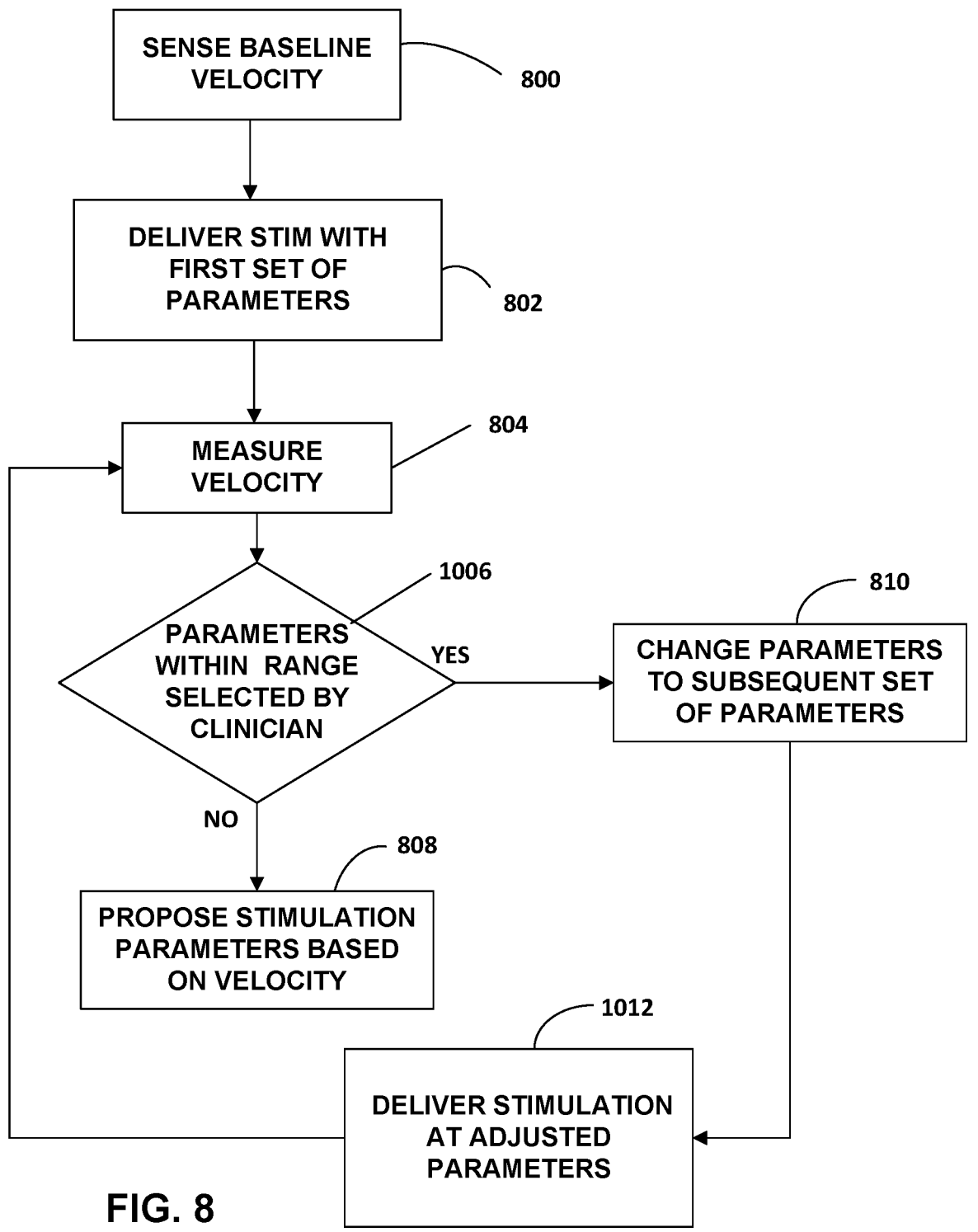
FIG. 8 is a flow diagram illustrating programming of one or more stimulation parameters based on sensed velocity information.

FIG. 8 is a flow diagram illustrating automated review of one or more stimulation parameters versus sensed velocity information to support programming of stimulation parameters. A programmer may shift through different parameter settings automatically or semi-automatically rather than the user manually selecting each of them.

Programmer may be used to determine efficacy of particular parameter settings of the IMD by testing parameter settings and recording velocity for each parameter setting, and giving a user an option to implement recommended parameter settings. The programmer automatically advances scanning through electrode pairs or parameter combinations to identify the stimulation parameters or electrode pairs that achieve a desired range of velocity values or exceeds a minimum change in velocity value.

In one or more examples, programmer directs the velocity sensor to sense and store a base line velocity for a patient without electrical stimulation (800). The base line velocity is prior to delivering stimulation. After the base line velocity is collected, stimulation is delivered to the patient with a first set of stimulation parameters (802), where the stimulation parameters include electrode combination, a polarity of each selected electrode, a voltage or current amplitude, a pulse width, and a pulse frequency. Upon delivery of the stimulation at the first set of stimulation parameters, patient ambulatory velocity is sensed for the stimulation parameter and velocity information is collected (804). In an example, the programmer evaluates a change in velocity as compared to the sensed baseline velocity. The velocity information and patient information are stored with the stimulation parameters, and the velocity information and patient information are output to the user.

The clinician may select a range of parameter values in which to apply and measure resulting velocity, and the programmer adjusts the parameter values through the range of parameters set by the clinician. If the parameter values are within the range set by the clinician (806), the programmer continues to adjust parameters to a subsequent set of parameters (810). For example, the programmer automatically selects a subsequent set of stimulation parameters and provides directions to the IMD to test the adjusted stimulation parameters by delivering stimulation with the adjusted stimulation parameters (812). For example, the programmer directs the IMD to deliver stimulation with an adjusted amplitude, for example with an amplitude different than the preliminary amplitude values. Upon delivery of the stimulation with the adjusted stimulation parameters, the velocity is sensed (804). If the parameters are not within the range set by the clinician, the programmer evaluates the achieved velocity values, and recommends stimulation parameters based on the velocity measurements (808).

The programmer continues to shift the stimulation parameters by either increasing or decreasing the stimulation parameter and collecting information regarding the respective velocity values. In an example, amplitude values can be modified, keeping the remaining stimulation parameters constant. While the example of amplitude is provided, the programmer may direct stimulation circuitry to step through various incremental settings of other stimulation parameters, such as stimulation pulse width, stimulation frequency, or duty cycle, and record the respective velocity information for each stepped value. The programmer may shift more than one stimulation parameter for each test and collect velocity information for the multiple shifted stimulation parameters. The stepped testing may occur for a predetermined number of shifts in stimulation parameters. For example, the individual stimulation parameters may each be tested ten times, shifting a certain percentage each time.

The techniques may be performed in a clinic, or on a remote location where a patient has an ability to check velocity with a velocity sensing device. The system allows for recording patient velocity as it corresponds with stimulation parameters without interacting with the patient for patient input, allowing the clinician to obtain objective efficacy information of the stimulation parameters.

Figure 9:
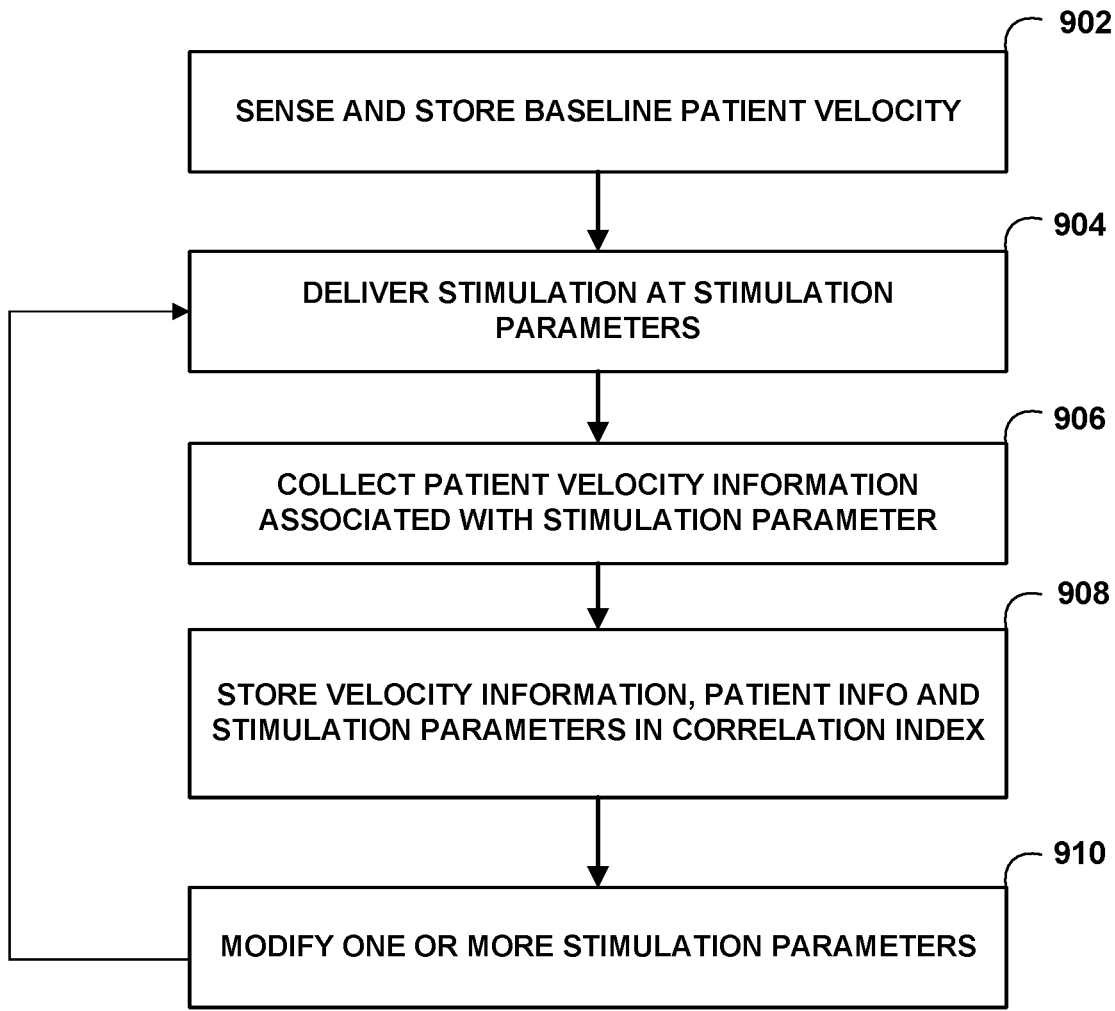
FIG. 9 is a flow diagram illustrating generation of index information based on correlation of one or more stimulation parameters and sensed velocity information.

FIG. 9 is a flow diagram illustrating generation of index information based on correlation of one or more stimulation parameters and sensed ambulatory velocity information. Information relating to velocity is stored over time as velocity information is collected during stimulation. The velocity information is stored by parameter settings and option patient information occurring during a particular parameter setting to achieve the velocity during stimulation. The information may be patient specific, or cover a population of patients with potentially related medical histories. The information may be used to develop a velocity correlation index which may be used in a closed loop setting, where it is possible to automatically update and adjust patient stimulation parameters for the IMD. The clinician programmer or another device may generate the correlation index and may download the index to the IMD, or the clinician programmer or another device generates and stores the index and uses the index to direct or control the IMD. The velocity correlation index may include a matrix of information that tracks a relationship between two or more variables. For example, the variables may include velocity information for stimulation using a set of stimulation parameters, and the stimulation parameters may include electrode positions, combinations and polarities, or stimulation amplitude, pulse width, pulse rate, or cycling. In an example, velocity data for each stimulation may be stored for each parameter setting. For example, a first velocity data is stored for stimulation with a first set of stimulation parameters, and a second velocity data is stored for stimulation for a second set of stimulation parameters. In addition, the velocity values may be compared to a baseline velocity value, and differences between the velocity values under stimulation and the baseline velocity may be stored in the velocity correlation index.

The first and second velocity values achieved using the first and second set of stimulation parameters may be further categorized within the velocity correlation index by additional factors such as factors dependent on the patient. Additional patient information can include factors such as time of day, or increments of time. The correlation index may include a log of velocity over time, and also after stimulation parameter settings have been adjusted.

The correlation index may include, as inputs, target velocity values and, as outputs, corresponding sets of stimulation parameters expected to produce the target velocity values. The outputs may be used to develop recommended parameters or parameters that are automatically implemented. For example, recommended parameter settings or automatically implemented parameters may indicate the stimulation to turn on for a certain period of time, and/or to turn off stimulation for a certain period of time. In another example, recommended duty cycle parameter settings may indicate stimulation to turn on for a period of time without creating desensitization of the stimulation. In one or more examples, the recommended parameter settings may indicate stimulation to occur at a certain time of day, for example when the patient is typically awake or active, or sleeping. In one or more examples, recommended parameter settings relate to when the patient has a certain posture, for example when the patient is in a supine position.

In one or more examples, developing the correlation index includes sensing and storing a base line velocity for a patient without electrical stimulation (902). The base line velocity is sensed prior to delivering stimulation. After the base line velocity is collected, stimulation is delivered to the patient at a set of stimulation parameters (904), where the stimulation parameters may include electrode combination, a voltage or current amplitude, a pulse width, and/or a pulse frequency. Upon delivery of the stimulation at the stimulation parameter, ambulatory velocity is sensed for the stimulation parameter and velocity information is collected (906). The velocity information and optional patient information are stored with the stimulation parameters within the correlation index (908). The stimulation parameters are modified (910), and the process is repeated to generate additional data to populate the correlation index.

The system may provide the clinician with the ability to adjust a timing of the parameter changes, how frequently parameter changes will occur within a specific time period. For instance, the clinician may provide input to select whether they want "gross resolution or fine resolution" to occur, pending degree of velocity change. The system may also provide the clinician with the ability to "guard rail" when the patient changes will occur due to velocity changes.

For instance, the system may receive input from the clinician indicating that parameter changes will occur only if the velocity changes +/−15% from current state (this could also be true velocity ranges (e.g., current velocity is X", change parameters if only if X falls below X=/−6").

The correlation index may further include a ranking of parameter candidates by program, such as velocity maximum or energy savings. For example, data in the index is grouped by greatest changes in velocity, or best energy savings. In some examples, sets of parameter settings may be grouped for achieving 25% or greater change in velocity from the baseline velocity, 50% change, or 100% change. In some examples, a clinician may set a program to prioritize these groupings for closed loop control. In some examples, the sets of parameter settings may be grouped by achieving low, medium or high energy conservation. The correlated data may be used by a closed loop control system to implement the most effective changes, while providing the patient the most significant achievements in ambulatory velocity.

The techniques of this disclosure enable several different ways of monitoring changes in velocity. For instance, as each leg of the patient moves independently, the system may monitor velocity changes for each leg individually or combined. This may apply in several scenarios, such as changes in distance covered within a given time period/distance, increase/decrease in stride frequency within a given time period/distance, increase/decrease in heel, toe, or heel-to-toe strikes within a given time period/distance, time between foot temporarily pausing on the ground between strides, time/velocity changes between stride lengths within a given time period/distance, changes in strides within a given time period/distance, and increase in velocity of the foot moving forward within a given time period/distance.

As natural arm swing mays when walking and typically relates to the lower legs, this disclosure proposed monitoring arm swing (e.g., as it relates to leg velocity). For instance, the system may monitor changes in arm swing when the patient is walking (e.g., as the human body naturally swings the opposite arm forward when walking/running within a given time period/distance). The system may utilize each of these to monitor the patient's ambulation.

While described above with reference to a single IMD, the techniques of this disclosure are not so limited. For instance, multiple IMDs (e.g., multiple DBS or other systems) may be implanted in a single patient and may be linked to a single velocity senor or multiple velocity sensors (e.g., shared velocity sensors). As one example, a patient may have one or more implants implanted with one or more leads per implant. In some of such examples, the sensor could be a central universal sensor or individual sensors that are attached to each leg/foot. If the patient has individual sensors on the lower extremities such that each leg could be "tuned" individually with programming (e.g., as, in DBS, the left hemisphere lead/s provide symptom control for the right side of the patient and vice versa). If the system includes a central based lead, the system may either modify both hemisphere one at a time or together. As another example, a patient may have two or more implants implanted. In some of such examples, the clinician may determine which programs/systems would be linked to the sensor data. For instance, the clinician may also use disease state/lead location to help determine which leads will utilize the data.

In some examples, the system may verify sensor integrity (e.g., during programming). For instance, if a link with the velocity sensor is lost, the system may refrain from making changes and/or inform the clinician of the link loss. In some cases, the clinician may determine whether the IMD should continue delivering stimulation using the most recent parameters or fall back to a safety programing until the link is restored.

The following numbered examples may illustrate one or more aspects of the disclosure:

Example 1. A system comprising: processing circuitry configured to: receive, with one or more processors, a first ambulatory velocity information of a patient while electrical stimulation with a first set of stimulation parameters is being delivered to the patient; adjust, based on the first ambulatory velocity information and by a predetermined amount, one or more of the first set of stimulation parameters to generate an adjusted set of stimulation parameters by a predetermined amount; receive, with the one or more processors, a subsequent ambulatory velocity information of the patient while the electrical stimulation with an adjusted set of stimulation parameters is being delivered to the patient; and generate, with the one or more processors and based on the subsequent ambulatory velocity, one or more recommended electrical stimulation parameters the patient.

Example 2. The system of example 1, wherein the one or more recommended parameters include one or more of stimulation amplitude, stimulation pulse width, stimulation frequency, or duty cycle.

Example 3. The system of example 1 or 2, wherein to adjust the one or more of the first set of stimulation parameters by a predetermined amount comprises adjust the one or more of the first set of stimulation parameters at a first rate until the subsequent ambulatory velocity is greater than the first ambulatory velocity.

Example 4. The system of example 3, wherein the first rate includes increasing amplitude 0.1 mA per 0.5 sec.

Example 5. The system of example 3, wherein the processing circuitry is further configured to adjust the one or more of the first set of stimulation parameters by a predetermined amount comprises to adjust the one or more of the first set of stimulation parameters at a second rate until the subsequent ambulatory velocity is less than or equal to the first ambulatory velocity.

Example 6. The system of example 5, wherein the second rate includes increasing amplitude 0.1 per second.

Example 7. The system of any of examples 1-6, wherein to receive the first ambulatory velocity or the subsequent ambulatory velocity comprises to sense the ambulatory velocity of the patient with a velocity sensing device a sensor attached to the patient.

Example 8. The system of example 7, wherein to sense the ambulatory velocity includes sensing with a sensor internal to the patient.

Example 9. The system of any of examples 1-8, wherein to receive the first ambulatory velocity or the subsequent ambulatory velocity comprises to sense ambulatory velocity of the patient with a velocity sensing device unattached to the patient.

Example 10. The system of example 9, wherein the velocity sensing device comprises a laser.

Example 11. The system of any of examples 1-10, wherein to receive the first ambulatory velocity or the subsequent ambulatory velocity comprises to sense with a first sensor internal to the patient and sensing with a second sensor unattached to the patient, and correlating the first sensor with the second sensor.

Example 12. The system of any of examples 1-11, wherein the processing circuitry is further configured to receive information relating to brain signal information of the patient upon delivery of the electrical stimulation with the first set of stimulation parameters to the patient.

Example 13. The system of any of examples 1-12, wherein the processing circuitry is further configured to generate a correlation index with the one or more processors that indexes the received ambulatory velocity information to one or more stimulation parameters of the electrical stimulation.

Example 14. The system of any of examples 1-13, wherein the processing circuitry is further configured to store data defining a correlation index defining a relationship between velocity information and parameter information for delivery of the electrical stimulation, wherein the processing circuitry automatically adjusts one or more of the parameters of the electrical stimulation based on the relationship automatically controls the electrical stimulation based on the adjusted parameters.

Example 15. A method comprising: receiving, with one or more processors, a first ambulatory velocity information of a patient while electrical stimulation with a first set of stimulation parameters is being delivered to the patient; adjusting, based on the first ambulatory velocity information and by a predetermined amount, one or more of the first set of stimulation parameters to generate an adjusted set of stimulation parameters by a predetermined amount; receiving, with the one or more processors, a subsequent ambulatory velocity information of the patient while the electrical stimulation with an adjusted set of stimulation parameters is being delivered to the patient; and generating, with the one or more processors and based on the subsequent ambulatory velocity, one or more recommended electrical stimulation parameters the patient.

Example 16. The method of example 15, wherein the one or more recommended parameters include one or more of stimulation amplitude, stimulation pulse width, stimulation frequency, or duty cycle.

Example 17. The method of example 15 or 16, wherein adjusting the one or more of the first set of stimulation parameters by a predetermined amount comprises adjusting the one or more of the first set of stimulation parameters at a first rate until the subsequent ambulatory velocity is greater than the first ambulatory velocity.

Example 18. The method of example 17, wherein the first rate includes increasing amplitude 0.1 mA per 0.5 sec.

Example 19. The method of any of examples 15-18, wherein receiving the first ambulatory velocity or the subsequent ambulatory velocity comprises sensing with a first sensor internal to the patient and sensing with a second sensor unattached to the patient, and correlating the first sensor with the second sensor.

Example 20. A computer-readable storage medium comprising: receive, with one or more processors, a first ambulatory velocity information of a patient while electrical stimulation with a first set of stimulation parameters is being delivered to the patient; adjust, based on the first ambulatory velocity information and by a predetermined amount, one or more of the first set of stimulation parameters to generate an adjusted set of stimulation parameters by a predetermined amount; receive, with the one or more processors, a subsequent ambulatory velocity information of the patient while the electrical stimulation with an adjusted set of stimulation parameters is being delivered to the patient; and generate, with the one or more processors and based on the subsequent ambulatory velocity, one or more recommended electrical stimulation parameters the patient.

The techniques described in this disclosure may be implemented, at least in part, in hardware, software, firmware or any combination thereof. For example, various aspects of the described techniques may be implemented within processing circuitry, which may include one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also form one or more processors or processing circuitry configured to perform one or more of the techniques of this disclosure.

Such hardware, software, and firmware may be implemented, and various operation may be performed within same device, within separate devices, and/or on a coordinated basis within, among or across several devices, to support the various operations and functions described in this disclosure. In addition, any of the described units, circuits or components may be implemented together or separately as discrete but interoperable logic devices. Depiction of different features as circuits or units is intended to highlight different functional aspects and does not necessarily imply that such circuits or units must be realized by separate hardware or software components. Rather, functionality associated with one or more circuits or units may be performed by separate hardware or software components or integrated within common or separate hardware or software components. Processing circuitry described in this disclosure, including a processor or multiple processors, may be implemented, in various examples, as fixed-function circuits, programmable circuits, or a combination thereof. Fixed-function circuits refer to circuits that provide particular functionality with preset operations. Programmable circuits refer to circuits that can be programmed to perform various tasks and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive stimulation parameters or output stimulation parameters), but the types of operations that the fixed-function circuits perform are generally immutable. In some examples, one or more of the units may be distinct circuit blocks (fixed-function or programmable), and in some examples, one or more of the units may be integrated circuits.

The techniques described in this disclosure may also be embodied or encoded in a computer-readable medium, such as a computer-readable storage medium, containing instructions that may be described as non-transitory media. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

What is claimed is:

1. A system comprising:
processing circuitry configured to:
    receive a first ambulatory velocity of a patient while electrical stimulation with a first set of stimulation parameters is being delivered to the patient;
    adjust, based on the first ambulatory velocity and by a predetermined amount, one or more of the first set of stimulation parameters to generate an adjusted set of stimulation parameters by the predetermined amount;
    receive a subsequent ambulatory velocity of the patient while the electrical stimulation with the adjusted set of stimulation parameters is being delivered to the patient, wherein to further adjust the one or more of the first set of stimulation parameters, the processing circuitry is configured to:
        automatically adjust the one or more of the first set of stimulation parameters at a first rate until the subsequent ambulatory velocity is greater than the first ambulatory velocity, wherein, to automatically adjust the one or more of the first set of stimulation parameters at the first rate, the processing circuitry is configured to increase an amplitude at a first amplitude increase rate; and
        automatically adjust the one or more of the first set of stimulation parameters at a second rate until the subsequent ambulatory velocity is less than or equal to the first ambulatory velocity, the first rate being different than the second rate, wherein, to automatically adjust the one or more of the first set of stimulation parameters at the second rate, the processing circuitry is configured to increase the amplitude at a second amplitude increase rate different than the first amplitude increase rate; and
    generate, based on the subsequent ambulatory velocity, one or more recommended electrical stimulation parameters for the patient; and
    cause delivery, to the patient, of electrical stimulation according to the one or more recommended electrical stimulation parameters.

2. The system of claim 1, wherein the one or more recommended parameters includes one or more of stimulation amplitude, stimulation pulse width, stimulation frequency, or duty cycle.

3. The system of claim 1, wherein the first amplitude increase rate is 0.1 mA per 0.5 sec.

4. The system of claim 1, wherein the second amplitude increase rate is 0.1 mA per second.

5. The system of claim 1, further comprising a velocity sensing device configured to sense the first ambulatory velocity or the subsequent ambulatory velocity of the patient, the velocity sensing device comprising a sensor configured to be attached to the patient.

6. The system of claim 5, wherein the sensor is configured to be disposed internal to the patient.

7. The system of claim 1, further comprising a velocity sensing device configured to sense the first ambulatory velocity or the subsequent ambulatory velocity of the patient, the velocity sensing device configured to be unattached to the patient.

8. The system of claim 7, wherein the velocity sensing device comprises a laser.

9. The system of claim 1, further comprising a first sensor configured to be internal to the patient and a second sensor configured to be unattached to the patient, wherein the first sensor is configured to output a first signal and the second sensor is configured to output a second signal, and wherein the processing circuitry is configured to correlate the first signal of the first sensor with the second signal of the second sensor as at least part of the first ambulatory velocity or the subsequent ambulatory velocity.

10. The system of claim 1, wherein the processing circuitry is further configured to receive information relating to brain signal information of the patient upon delivery of the electrical stimulation with the first set of stimulation parameters to the patient.

11. A method comprising:
    receiving, with one or more processors, a first ambulatory velocity of a patient while electrical stimulation with a first set of stimulation parameters is being delivered to the patient;
    adjusting, based on the first ambulatory velocity and by a predetermined amount, one or more of the first set of stimulation parameters to generate an adjusted set of stimulation parameters by the predetermined amount;
    receiving a subsequent ambulatory velocity of the patient while the electrical stimulation with the adjusted set of stimulation parameters is being delivered to the patient, wherein further adjusting the one or more of the first set of stimulation parameters comprises:
        automatically adjusting the one or more of the first set of stimulation parameters at a first rate until the subsequent ambulatory velocity is greater than the first ambulatory velocity, wherein automatically adjusting the one or more of the first set of stimulation parameters at the first rate includes increasing an amplitude at a first amplitude increase rate; and
        automatically adjusting the one or more of the first set of stimulation parameters at a second rate until the subsequent ambulatory velocity is less than or equal to the first ambulatory velocity, the first rate being different than the second rate, wherein automatically adjusting the one or more of the first set of stimulation parameters at the second rate includes increasing the amplitude at a second amplitude increase rate different than the first amplitude increase rate;
    generating, and based on the subsequent ambulatory velocity, one or more recommended electrical stimulation parameters the patient; and
    causing delivery, to the patient, of electrical stimulation with the one or more recommended electrical stimulation parameters.

12. The method of claim 11, wherein the one or more recommended parameters include one or more of stimulation amplitude, stimulation pulse width, stimulation frequency, or duty cycle.

13. The method of claim 11, wherein the first amplitude increase rate is 0.1 mA per 0.5 sec.

14. The method of claim 11, further comprising:
    sensing a first signal with a first sensor internal to the patient; and
    sensing a second signal with a second sensor unattached to the patient; and
    correlating the first signal of the first sensor with the second signal of the second sensor as at least part of the first ambulatory velocity or the subsequent ambulatory velocity.

15. A non-transitory computer-readable storage medium comprising instructions that, when executed, cause one or more processors to:

receive a first ambulatory velocity of a patient while electrical stimulation with a first set of stimulation parameters is being delivered to the patient;

adjust, based on the first ambulatory velocity and by a predetermined amount, one or more of the first set of stimulation parameters to generate an adjusted set of stimulation parameters by the predetermined amount;

receive a subsequent ambulatory velocity of the patient while the electrical stimulation with the adjusted set of stimulation parameters is being delivered to the patient, wherein the instructions that cause the one or more processors to further adjust the one or more of the first set of stimulation parameters comprise instructions that cause the one or more processors to:

automatically adjust the one or more of the first set of stimulation parameters at a first rate until the subsequent ambulatory velocity is greater than the first ambulatory velocity, wherein the instructions that cause the one or more processors to automatically adjust the one or more of the first set of stimulation parameters at the first rate comprise instructions that cause the one or more processors to increase an amplitude at a first amplitude increase rate; and automatically adjust the one or more of the first set of stimulation parameters at a second rate until the subsequent ambulatory velocity is less than or equal to the first ambulatory velocity, the first rate being different than the second rate, wherein the instructions that cause the one or more processors to automatically adjust the one or more of the first set of stimulation parameters at the second rate comprise instructions that cause the one or more processors to increase the amplitude at a second amplitude increase rate different than the first amplitude increase rate;

generate, based on the subsequent ambulatory velocity, one or more recommended electrical stimulation parameters the patient; and cause delivery, to the patient, of electrical stimulation with the one or more recommended electrical stimulation parameters.

* * * * *